US007897376B2

(12) United States Patent
Porter et al.

(10) Patent No.: US 7,897,376 B2
(45) Date of Patent: Mar. 1, 2011

(54) METHOD FOR EXTRACTING A TARGET PRODUCT FROM A HOST CELL EMPLOYING ZWITTERIONIC DETERGENT COMBINATIONS

(75) Inventors: Jeff Porter, Manchester, MO (US); Richard Mehigh, St. Louis, MO (US)

(73) Assignee: Sigma-Aldrich Co., St. Louis, MO (US)

( * ) Notice: Subject to any disclaimer, the term of this patent is extended or adjusted under 35 U.S.C. 154(b) by 681 days.

(21) Appl. No.: 11/850,813

(22) Filed: Sep. 6, 2007

(65) Prior Publication Data
US 2008/0064093 A1 Mar. 13, 2008

Related U.S. Application Data

(62) Division of application No. 11/210,178, filed on Aug. 23, 2005, now Pat. No. 7,282,475.

(60) Provisional application No. 60/604,272, filed on Aug. 25, 2004.

(51) Int. Cl.
C11D 1/92 (2006.01)

(52) U.S. Cl. ...................... 435/270; 435/287.2; 510/424; 510/504

(58) Field of Classification Search .................. 510/424, 510/504; 435/270, 287.2
See application file for complete search history.

(56) References Cited

U.S. PATENT DOCUMENTS

| | | |
|---|---|---|
| 3,642,450 A | 2/1972 | Eriksson |
| 4,032,663 A | 6/1977 | Kobayashi et al. |
| 4,525,452 A | 6/1985 | Jones et al. |
| 4,554,248 A | 11/1985 | Green et al. |
| 4,569,794 A | 2/1986 | Smith et al. |
| 4,703,004 A | 10/1987 | Hopp et al. |
| 4,851,341 A | 7/1989 | Hopp et al. |
| 4,859,613 A | 8/1989 | Lawrence |
| 5,011,912 A | 4/1991 | Hopp et al. |
| 5,047,513 A | 9/1991 | Dobeli et al. |
| 5,104,789 A | 4/1992 | Permar et al. |
| 5,310,663 A | 5/1994 | Dobeli et al. |
| 5,506,121 A | 4/1996 | Skerra et al. |
| 5,536,419 A | 7/1996 | Escalona et al. |
| 5,536,450 A | 7/1996 | Masters et al. |
| 5,585,273 A | 12/1996 | Lawrence et al. |
| 5,594,115 A | 1/1997 | Sharma |
| 5,624,711 A | 4/1997 | Sundberg et al. |
| 5,648,527 A | 7/1997 | Prossel et al. |
| 5,648,528 A | 7/1997 | Prossel et al. |
| 5,654,176 A | 8/1997 | Smith |
| 5,807,690 A | 9/1998 | Sanders et al. |
| 5,837,529 A | 11/1998 | Wan et al. |
| 5,888,834 A | 3/1999 | Ishikawa et al. |
| 5,922,534 A | 7/1999 | Lichtenwalter |
| 5,985,593 A | 11/1999 | Thornton et al. |
| 5,989,431 A | 11/1999 | Evans et al. |
| 5,998,155 A | 12/1999 | Burton et al. |
| 6,040,182 A | 3/2000 | Septak |
| 6,042,710 A | 3/2000 | Dubrow |
| 6,105,786 A | 8/2000 | Braunstein et al. |
| 6,106,779 A | 8/2000 | Buechler et al. |
| 6,174,704 B1 | 1/2001 | Chu et al. |
| 6,174,729 B1 | 1/2001 | Alam |
| 6,255,053 B1 | 7/2001 | Lichtenwalter |
| 6,268,191 B1 | 7/2001 | Prud'homme et al. |
| 6,277,648 B1 | 8/2001 | Colpan |
| 6,309,827 B1 | 10/2001 | Goldstein et al. |
| 6,331,254 B1 | 12/2001 | White et al. |
| 6,344,343 B1 | 2/2002 | Staehelin et al. |
| 6,348,318 B1 | 2/2002 | Valkirs |
| 6,383,810 B2 | 5/2002 | Fike et al. |
| 6,403,382 B1 | 6/2002 | Zhu et al. |
| 6,406,840 B1 | 6/2002 | Li et al. |
| 6,413,784 B1 | 7/2002 | Lundsgaard et al. |
| 6,461,154 B2 | 10/2002 | Piringer et al. |
| 6,596,532 B1 | 7/2003 | Hyman et al. |
| 6,623,655 B1 | 9/2003 | Kappel et al. |
| 6,723,510 B2 | 4/2004 | Lubenow et al. |
| 6,897,037 B2 | 5/2005 | Okada et al. |
| 7,094,742 B2 | 8/2006 | Gaudreault |
| 7,138,268 B2 | 11/2006 | Lichtenwalter |
| 7,183,073 B2 | 2/2007 | Hyman et al. |
| 7,282,475 B2 | 10/2007 | Porter et al. |
| 7,285,641 B2 | 10/2007 | Fu et al. |
| 7,615,616 B2 | 11/2009 | Hook et al. |
| 2002/0012982 A1 | 1/2002 | Blakesley et al. |
| 2002/0061599 A1 | 5/2002 | Elling et al. |
| 2002/0127587 A1 | 9/2002 | Simms et al. |
| 2003/0032013 A1 | 2/2003 | Dapron et al. |

(Continued)

FOREIGN PATENT DOCUMENTS

EP          0441469 A1    8/1991

(Continued)

OTHER PUBLICATIONS

Andrews et al., Enzymatic lysis and disruption of microbial cells, Trends in Biotechnology, 1987, pp. 273-277, vol. 5. Becker et al., Downstream Process of Proteins, Biotech Advs, 1983, pp. 247-261, vol. 1.
Coakley et al., Disruption of Micro-Organisms, Advances in Microbial Physiology, 1977, pp. 279-341, vol. 16.
Wiseman, Enzymes for Breakage of Micro-organisms, Process Biochemistry, 1969, pp. 63-65, vol. 4, No. 5.
Wolska-Mitaszko et al., An Efficient Technique for the Isolation of Yeast Spores and the Preparation of Sheroplast Lysates Active in Protein Synthesis, Analytical Biochemistry, 1981, pp. 241-247, vol. 116.
International Search Report for PCT/US05/29857 dated Nov. 29, 2005; 2 pages.

(Continued)

Primary Examiner — Charles I Boyer
(74) Attorney, Agent, or Firm — Polsinelli Shughart PC

(57) ABSTRACT

The present invention provides lysis reagents, containers, methods and kits relating to the extraction or the extraction and isolation of a cellular component from a host cell. More specifically, the invention provides combinations of zwitterionic compounds that may be employed to aide in the extraction or the extraction and isolation of a cellular component from a host cell.

28 Claims, 6 Drawing Sheets

U.S. PATENT DOCUMENTS

| | | | |
|---|---|---|---|
| 2004/0180445 A1* | 9/2004 | Domanico et al. | 436/17 |
| 2004/0259162 A1* | 12/2004 | Kappel et al. | 435/7.1 |
| 2005/0137114 A1 | 6/2005 | Gatlin et al. | |
| 2005/0221368 A1 | 10/2005 | Rana | |

FOREIGN PATENT DOCUMENTS

| | | |
|---|---|---|
| WO | 8604421 A1 | 7/1986 |
| WO | 9004411 A1 | 5/1990 |
| WO | 9918433 A1 | 4/1999 |
| WO | 0159060 A2 | 8/2001 |
| WO | 0181365 A2 | 11/2001 |
| WO | 0183805 A2 | 11/2001 |
| WO | 03023050 A2 | 3/2003 |

OTHER PUBLICATIONS

International Search Report for PCT/US04/13767 dated Jan. 21, 2005, 2 pages.

Supplementary European Search Report for EP04751252 dated Apr. 26, 2007, 2 pages.

www.merriam-webster.com/dictionary/coat, 2 pages, downloaded Mar. 28, 2010.

The Express Kits, Product Information, http://rnature.com/productinfo.html, Jul. 22, 2002, 10 pages.

Hughes et al, The Disintegration of Micro-organisms, Methods in Microbiology, 1969, pp. 1-54, vol. B.

Karlsson et al, Binding and detection of glycosaminoglycans immobilized on membranes treated with cationic detergents, Anal Biochem, 2000, pp. 51-58, vol. 286.

Miozzari et al., Permeabilization of Microorganisms by Triton X-100, Analytical Biochemistry, 1978, pp. 220-233, vol. 90.

Novagen, Inc., Popculture (TM) Reagent Product Brochure, 4 pages.

Schutte et al, Pilot and Process Scale Techiques for Cell Disruption, Biotechnology and Applied Biochemistry, 1990, pp. 599-620, vol. 12.

University of Capetown website, http://www.uct.ac.za/depts/mmi/bbp/help/bac1.htm, Jul. 22, 2002, 10 pages.

University of Capetown website, http://www.uct.ac.za/depts/mmi/bbhelp/rec1.html, Jul. 22, 2002, 12 pages.

Non-Final Office Action for U.S. Appl. No. 10/837,776 dated Jul. 8, 2010, 15 pages.

Final Office Action for U.S. Appl. No. 10/837,776 dated Apr. 7, 2010, 9 pages.

Non-Final Office Action for U.S. Appl. No. 10/837,776 dated Sep. 30, 2009, 10 pages.

Non-Final Office Action for U.S. Appl. No. 10/837,776 dated Mar. 6, 2009, 9 pages.

Final Office Action for U.S. Appl. No. 10/837,776 dated Apr. 7, 2008, 7 pages.

Non-Final Office Action for U.S. Appl. No. 10/837,776 dated Jul. 6, 2007, 8 pages.

* cited by examiner

```
                       SEQUENCE LISTING

<160> NUMBER OF SEQ ID NOS: 3

<210> SEQ ID NO 1
<211> LENGTH: 8
<212> TYPE: PRT
<213> ORGANISM: Artificial
<220> FEATURE:
<223> OTHER INFORMATION: FLAG EPITOPE TAG

<400> SEQUENCE: 1

Asp Tyr Lys Asp Asp Asp Asp Lys
1               5

<210> SEQ ID NO 2
<211> LENGTH: 8
<212> TYPE: PRT
<213> ORGANISM: Artificial
<220> FEATURE:
<223> OTHER INFORMATION: INVITROGEN EPITOPE TAG

<400> SEQUENCE: 2

Asp Leu Tyr Asp Asp Asp Asp Lys
1               5

<210> SEQ ID NO 3
<211> LENGTH: 23
<212> TYPE: PRT
<213> ORGANISM: Artificial
<220> FEATURE:
<223> OTHER INFORMATION: FLAG 3X EPITOPE TAG

<400> SEQUENCE: 3

Met Asp Tyr Lys Asp His Asp Gly Asp Tyr Lys Asp His Asp Ile Asp
1               5                   10                  15

Tyr Lys Asp Asp Asp Asp Lys
            20
```

METHOD FOR EXTRACTING A TARGET PRODUCT FROM A HOST CELL EMPLOYING ZWITTERIONIC DETERGENT COMBINATIONS

CROSS REFERENCE TO RELATED APPLICATIONS

This application is a divisional application of U.S. patent application Ser. No. 11/210,178, filed on Aug. 23, 2005, which claims priority from U.S. Provisional Application Ser. No. 60/604,272, filed on Aug. 25, 2004, each of which is hereby incorporated by reference in its entirety.

FIELD OF THE INVENTION

The present invention relates to lysis reagents, containers, methods, and kits for use in the extraction or the extraction and isolation of a target product from a host cell. More specifically, the invention provides combinations of zwitterionic compounds that comprise a detergent composition that may be employed in methods for use in the extraction or the extraction and isolation of a target product from a host cell.

BACKGROUND OF THE INVENTION

Advances in biotechnology have made it possible to produce large quantities of macromolecules such as nucleic acids, proteins and peptides in a variety of host cells. But disadvantageously, the extraction and isolation of these macromolecules from their host cells has thus far been a multi step process, involving a first step, lysis, to free the macromolecules from their cellular confines, and then one or more subsequent steps to separate the target product from other cellular components.

A variety of techniques have been used to lyse cells, each having certain advantages and disadvantages. One such technique is mechanical or physical disruption of cell membranes. For example, sonication, French cell press, homogenization, grinding, freeze-thaw lysis, and various other methods of physically or mechanically lysing cells have been employed. But mechanical lysis requires specialized equipment that may not be readily available and is also extremely labor intensive. Equally, sonication generates heat that may denature the target polypeptide or protein. Each of these mechanical or physical techniques also results in a relatively low yield of the target product. Moreover, mechanical or physical lysis steps are also difficult to automate and miniaturize for the purpose of purifying small amounts of several proteins in parallel.

Enzymes and detergents have also been used to enzymatically or chemically lyse cells. But as with mechanical and physical lysis, enzymatic or chemical lysis also has several inherent drawbacks. Often the addition of an enzyme or detergent solution results in a dilution of the solution containing the cells to be lysed. In addition, the desired product must still be separated from the resulting membrane fragments, undesired proteins, and other cellular debris. For example, two widely utilized kits for detergent-aided purification include BugBuster® (Novagen) and B-PER (Pierce). Both of these kits use a detergent solution to disrupt the cell membrane and resultantly, release the cellular components including the target product. But neither method couples a purification step with the lysis step. The BugBuster® product, in fact, utilizes a benzonase nuclease to decrease the viscosity in the lysate due to the large amounts of chromosomal DNA present in the sample after lysis. But the product does not include any method for removal of the small DNA fragments that are necessarily generated by the nuclease digestion. The B-PER product is solely intended as an extraction system. The system includes a centrifugation step, which removes some insoluble debris; however, there is no subsequent purification of the target product from the rest of the cellular material. Any contamination of the lysates generated with the B-PER product must be removed using separate methods of purification. Analogous to mechanical or physical lysis, enzymatic or chemical lysis, as detailed above, is often labor intensive, and may result in relatively low target product yields.

Utilizing current technology, after the target product has been released from the cell by lysis, as detailed above, it is then typically purified from other cellular components. A variety of affinity capture methods have been utilized to purify proteins, peptides and nucleic acids. U.S. Pat. Nos. 4,569,794, 5,310,663, and 5,594,115 describe the use of metal chelating peptides, which include histidine residues, and their use in protein purification. Alternatively, U.S. Pat. Nos. 4,703,004, 4,851,341, 5,011,912, and 6,461,154 describe the antigenic FLAG® peptide, and the purification of proteins comprising the peptide. U.S. Pat. No. 5,654,176 describes the use of glutathione-S-transferase for the purification of proteins. U.S. Pat. No. 5,998,155 describes the use of an avidin/biotin capture system. In each of these instances, the interaction between an affinity tag or sequence on the target product and the corresponding ligand results in the "capture" of the target product. Unbound compositions and other cellular debris can then be washed away, leaving the target product bound to the tag or sequence-specific ligand. A specific eluant is then used to release the bound target product, resulting in a purified target product.

But disadvantageously, the multiple steps involved in first lysing a host cell and then purifying the target product increases the cost and time required for isolating the product, especially in high throughput applications. Moreover, in addition to being labor intensive, current lysis techniques often result in a relatively low yield of target product.

SUMMARY OF THE INVENTION

Among the several aspects of the current invention, therefore, is the provision of methods for using a detergent composition to extract or extract and isolate a target product from a host cell. Advantageously, when the detergent composition is utilized in a well or container, the need to centrifuge a cellular solution that has been subjected to lysis is eliminated. Furthermore, if the well or container also comprises a capture ligand, it may be employed as a part of a one step process to extract and isolate a target product from a host cell.

Accordingly, one aspect of the present invention encompasses a method for extracting a target product from a host cell. The method comprises contacting the host cell with a detergent composition comprising at least two different compounds, each of the two compounds having at least one quaternary amine and at least one sulfonate ion. The method further comprises lysing the host cell to release the target product from the cell and form cellular debris.

Yet another aspect of the invention encompasses a well for the extraction of a target product from a host cell. The well contains a detergent composition that comprises at least two different compounds, each of the two compounds having at least one quaternary amine and at least one sulfonate ion.

A further aspect of the invention provides a kit for the extraction and isolation of a target product from a host cell. The kit comprises a well containing a detergent composition and a capture ligand. The detergent composition comprises at least two different compounds, each of the two compounds having at least one quaternary amine and at least one sulfonate ion. The capture ligand may be a metal chelate, glutathione, biotin, streptavidin, an antibody, a charged particle, and an insoluble hydrophobic group. The kit also comprises instructions for the extraction and isolation of the target product from the host cell.

Other objects and features of the invention will be in part apparent and in part pointed out hereinafter.

DETAILED DESCRIPTION OF THE PREFERRED EMBODIMENTS

Figure 1:
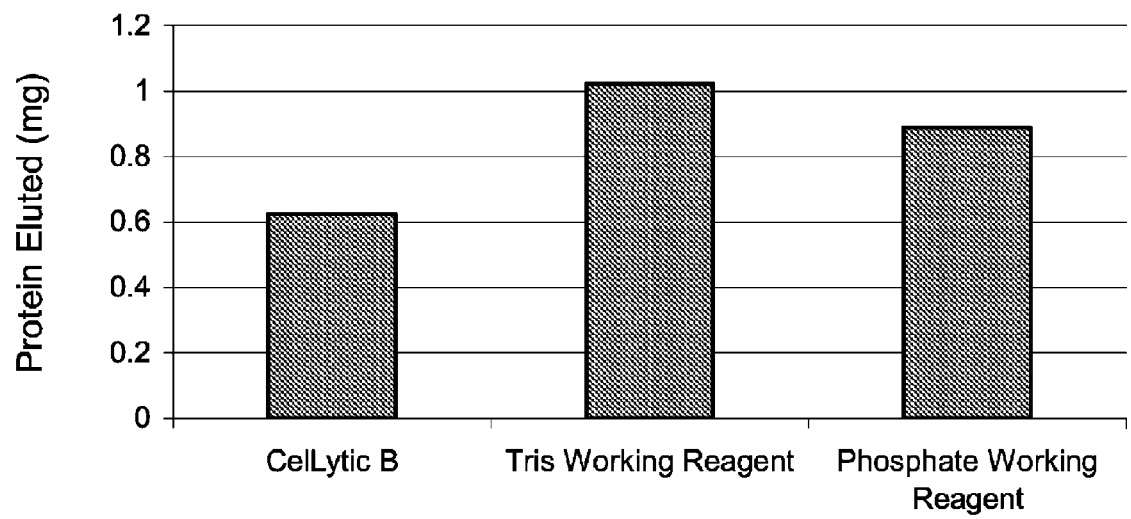
FIG. 1 depicts a graph showing a comparison of the amount of protein recovered after host cells were lysed with either the commercially available CelLytic B (Sigma-Aldrich Co. Product No. B3553), or the zwitterionic detergent combination of 3-(N,N-Dimethyltetradecylammonio)propanesulfonate (Sigma-Aldrich Co. Product No. T7763) and C7BzO (Sigma-Aldrich Co. Product No. C0856) in either a Tris based buffer (Tris Working Reagent") or a phosphate based buffer (i.e., "Phosphate Working Reagent"). Samples were affinity purified using HIS-Select nickel spin columns.

The present invention provides novel combinations of compounds that may be utilized to lyse the membrane of a host cell. Generally speaking, the combinations of the invention may be employed as a detergent blend to aid in the purification of a target product, such as a protein, nucleic acid or polypeptide, from a host cell. Advantageously, as illustrated in the examples, use of the detergent combinations of the present invention result in significantly higher yields of target product compared to other commercially available lysis reagents, including CelLytic B, BugBuster® and B-PER and compared to mechanical lysis.

Detergent Compositions

One aspect of the current invention, therefore, encompasses the use of compounds that are detergents and that, when used in combination, as detailed in the examples, result in significantly higher yields of target product compared to either detergent used alone, compared to other commercially available enzymatic or chemical lysis reagents or compared to mechanical or physical lysis. In one embodiment, the composition will comprise at least two different compounds where each compound has at least one quaternary amine and at least one sulfonate ion. In an exemplary embodiment, each of the compounds in the composition will have one quaternary amine and one sulfonate ion. Typically, in each of these embodiments, the compounds comprising the composition are in a zwitterionic state when at or near a physiological pH.

In yet another embodiment, the invention encompasses a composition comprising at least two different compounds that are selected from the group of compounds having formula (Ia):

wherein, $R^1$, $R^2$, $R^3$, and $R^4$ are independently hydrocarbyl or substituted hydrocarbyl.

Typically, for compounds having formula (Ia) each of $R^1$, $R^2$, and $R^3$ will consist of a chain of no more than about 1 to 10 atoms, more preferably a chain of about 1 to 7 atoms, still more preferably, a chain of no more than 1 to 5 atoms and even more preferably, a chain of no more than 1 to 3 atoms. In most embodiments for compounds having formula (Ia), $R^4$ will consist of a chain of no more than about 5 to 30 atoms, more preferably, a chain of about 8 to about 25 atoms, and still more preferably, will be a chain of about 10 to about 20 atoms. Exemplary compounds having formula (Ia) will have a chain of about 1 to 5 atoms for each of $R^1$, $R^2$, and $R^3$ and a chain of about 8 to 20 atoms for $R^4$. More exemplary compounds having formula (Ia) will have a methyl group for each of $R^1$ and $R^2$, a chain from about 2 to 5 atoms for $R^3$ and a chain from about 10 to 16 atoms for $R^4$. Even more exemplary compounds having formula (Ia) will have a methyl group for each of $R^1$ and $R^2$, a chain from about 1 to 3 atoms for $R^3$ and a chain from about 10 to 16 atoms for $R^4$.

A further embodiment encompasses a composition comprising at least two different compounds that are selected from the group of compounds having formula (Ib):

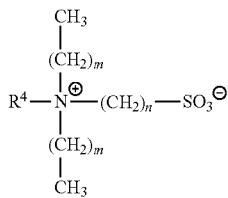

(Ib)

wherein, m is an integer from 0 to 10; n is an integer from 1 to 10; and $R^4$ is a hydrocarbyl or substituted hydrocarbyl.

Generally speaking, in most embodiments for compounds having formula (Ib), m is an integer from 0 to 5, n is an integer from 1 to 8 and $R^4$ has a chain length of from about 8 to 25 atoms. In a more exemplary alternative of this embodiment, m is an integer from 0 to 3, n is an integer from 1 to 5 and $R^4$ has a chain length of from about 10 to 20 atoms. In an even more exemplary alternative of this embodiment, m is 0, n is 3 and $R^4$ has a chain length from about 10 to 16 atoms.

Yet another embodiment encompasses a composition comprising at least two different compounds that are selected from the group of compounds having formula (Ic):

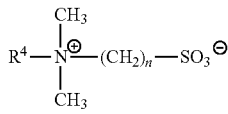

(Ic)

wherein, n is an integer from 1 to 10; and $R^4$ is a hydrocarbyl or substituted hydrocarbyl.

Typically for compounds having formula (Ic), n is an integer from 1 to 8 and $R^4$ has a chain length of from about 8 to 25 atoms. In a more exemplary alternative of this embodiment, n is an integer from 1 to 5 and $R^4$ has a chain length of from about 10 to 20 atoms. In an even more exemplary alternative of this embodiment, n is 3 and $R^4$ has a chain length from about 10 to 16 atoms.

A further embodiment encompasses a composition comprising at least one compound that is selected from the group of compounds having formula (Ic) as described in any of the embodiments above and at least one other compound that is selected from the group of compounds having formula (Id):

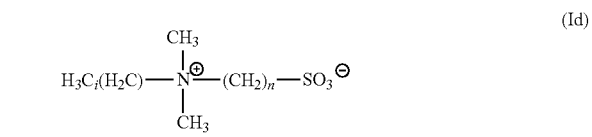

(Id)

wherein, i is an integer from 8 to 25; and n is an integer from 1 to 10.

Generally speaking, in most embodiments for compounds having formula (Id), i is an integer from 10 to 20, and n is an integer from 1 to 5. In an exemplary embodiment, i is an integer from 10 to 16, and n is 3.

Other detergent compositions suitable for use in the present invention are detailed in Table A.

TABLE A

| Compound No. 1 | Compound No. 2 |
|---|---|
| A compound having formula (Ia) | A compound having formula (Ia) |
| A compound having formula (Ia) | A compound having formula (Ib) |
| A compound having formula (Ia) | A compound having formula (Ic) |
| A compound having formula (Ia) | A compound having formula (Id) |
| A compound having formula (Ib) | A compound having formula (Ib) |
| A compound having formula (Ib) | A compound having formula (Ic) |
| A compound having formula (Ib) | A compound having formula (Id) |
| A compound having formula (Ic) | A compound having formula (Ic) |
| A compound having formula (Ic) | A compound having formula (Id) |
| A compound having formula (Id) | A compound having formula (Id) |

In one preferred embodiment, the detergent composition will include at least two compounds selected from the group consisting of 3-(N,N-Dimethyltetradecylammonio)propanesulfonate (SB3-14); 3-(4-Heptyl)phenyl-3-hydroxypropyl)dimethylammoniopropanesulfonate (C7BzO); CHAPS (3-[(3-cholamidopropyl)dimethylammonio]-1-propanesulfonate); CHAPSO (3-[(3-cholamidopropyl)dimethylammonio]-2-hydroxy-1-propanesulfonate); 3-(decyldimethylammonio)propanesulfonate inner salt (SB3-10); 3-(dodecyldimethylammonio)propanesulfonate inner salt (SB3-12); 3-(N,N-dimethyloctadecylammonio)propanesulfonate (SB3-18); 3-(N,N-dimethyloctylammonio)propanesulfonate inner salt (SB3-8); 3-(N,N-dimethylpalmitylammonio)propanesulfonate (SB3-16); and 3-[N,N-dimethyl(3-myristoylaminopropyl)ammonio]propanesulfonate (ASB-14).

In a more preferred embodiment, the detergent composition will include at least two compounds selected from the group consisting of 3-(N,N-Dimethyltetradecylammonio)propanesulfonate (SB3-14); 3-(4-Heptyl)phenyl-3-hydroxypropyl)dimethylammoniopropanesulfonate (C7BzO); 3-(dodecyldimethylammonio)propanesulfonate inner salt (SB3-12); and 3-[N,N-dimethyl(3myristoylaminopropyl)ammonio]propanesulfonate (ASB-14).

In a particularly preferred embodiment, the detergent composition will comprise 3-(N,N-Dimethyltetradecylammonio)propanesulfonate (SB3-14; Sigma-Aldrich Co. Product No. T7763) and 3-(4-Heptyl)phenyl-3-hydroxypropyl)dimethylammoniopropanesulfonate (C7BzO; Sigma-Aldrich Co. Product No. C0856). These compounds have the following formulas:

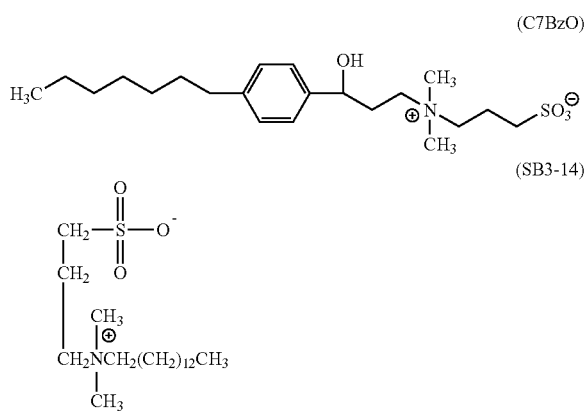

(C7BzO)

(SB3-14)

Other suitable detergent compositions for use in the invention include any of the combinations listed in Table B.

TABLE B

| Compound No. 1 | Compound No. 2 |
|---|---|
| SB3-14 | C7BzO |
| SB3-14 | CHAPS |
| SB3-14 | CHAPSO |
| SB3-14 | SB3-10 |
| SB3-14 | SB3-12 |
| SB3-14 | SB3-18 |
| SB3-14 | SB3-8 |
| SB3-14 | SB3-16 |
| SB3-14 | ASB-14 |
| C7BzO | CHAPS |
| C7BzO | CHAPSO |
| C7BzO | SB3-10 |
| C7BzO | SB3-12 |
| C7BzO | SB3-18 |
| C7BzO | SB3-8 |
| C7BzO | SB3-16 |
| C7BzO | ASB-14 |
| CHAPS | CHAPSO |
| CHAPS | SB3-10 |
| CHAPS | SB3-12 |
| CHAPS | SB3-18 |
| CHAPS | SB3-8 |
| CHAPS | SB3-16 |
| CHAPS | ASB-14 |
| CHAPSO | SB3-10 |
| CHAPSO | SB3-12 |
| CHAPSO | SB3-18 |
| CHAPSO | SB3-8 |
| CHAPSO | SB3-16 |
| CHAPSO | ASB-14 |
| SB3-10 | SB3-12 |
| SB3-10 | SB3-18 |
| SB3-10 | SB3-8 |
| SB3-10 | SB3-16 |
| SB3-10 | ASB-14 |
| SB3-12 | SB3-18 |
| SB3-12 | SB3-8 |
| SB3-12 | SB3-16 |
| SB3-12 | ASB-14 |
| SB3-18 | SB3-8 |
| SB3-18 | SB3-16 |
| SB3-18 | ASB-14 |
| SB3-8 | SB3-16 |
| SB3-8 | ASB-14 |
| SB3-16 | ASB-14 |

Generally speaking, any of the detergent compositions described above having at least two different compounds where each compound has at least one quaternary amine and at least one sulfonate ion (e.g. compounds having any of formulas (Ia), (Ib), (Ic), or (Id)) possess certain physiochemical properties that aid in the extraction of a target product, such as a peptide, protein or nucleic acid, from a host cell. For example, a suitable detergent composition will typically retain its zwitterionic state at a pH of approximately 2 to 12, more preferably, the composition will retain its zwitterionic state at a pH of approximately 4 to 10, and even more preferably, the composition will retain its zwitterionic state at a pH of approximately 6 to 9.

In general, it is also contemplated that any of the detergent compositions of the invention may be combined with one or more additional agents. As utilized herein, detergent composition shall mean either any of the detergent combinations detailed above, such as in Tables A or B, or such detergent combinations along with any additional agents described herein. These agents can and will vary depending upon the particular embodiment. For example, the detergent composition of the invention may optionally comprise additional detergents, a lytic enzyme, a chaotropic reagent, or combinations thereof. By way of further example, the detergent composition of the invention may further comprise buffers, antifoaming agents, bulking agents, processing enzymes, enzymatic inhibitors, or other additives that aid in the extraction and isolation of the target product, such as peptides, proteins, or nucleic acids.

In one embodiment, the detergent composition of the invention may optionally include one or more additional detergents. A variety of such additional detergents are suitable for use in the present invention including anionic, cationic, non-ionic, and zwitterionic detergents. Exemplary detergents include chenodeoxycholic acid; chenodeoxycholic acid sodium salt; cholic acid; dehydrocholic acid; deoxycholic acid; deoxycholic acid methyl ester; digitonin; digitoxigenin; N,N-dimethyldodecylamine oxide; docusate sodium salt; glycochenodeoxycholic acid sodium salt; glycocholic acid hydrate; glycocholic acid sodium salt hydrate; glycodeoxycholic acid monohydrate; glycodeoxycholic acid sodium salt; glycolithocholic acid 3-sulfate disodium salt; glycolithocholic acid ethyl ester; N-lauroylsarcosine sodium salt; N-lauroylsarcosine; lithium dodecyl sulfate; lugol solution; Niaproof 4, Type 4 (i.e., 7-ethyl-2-methyl-4-undecyl sulfate sodium salt; sodium 7-ethyl-2-methyl-4-undecyl sulfate); 1-octanesulfonic acid sodium salt; sodium 1-butanesulfonate; sodium 1-decanesulfonate; sodium 1-dodecanesulfonate; sodium 1-heptanesulfonate anhydrous; sodium 1-nonanesulfonate; sodium 1-propanesulfonate monohydrate; sodium 2-bromoethanesulfonate; sodium cholate hydrate; sodium choleate; sodium deoxycholate; sodium deoxycholate monohydrate; sodium dodecyl sulfate; sodium hexanesulfonate anhydrous; sodium octyl sulfate; sodium pentanesulfonate anhydrous; sodium taurocholate; sodium taurodeoxycholate; saurochenodeoxycholic acid sodium salt; taurodeoxycholic acid sodium salt monohydrate; taurohyodeoxycholic acid sodium salt hydrate; taurolithocholic acid 3-sulfate disodium salt; tauroursodeoxycholic acid sodium salt; Trizma® dodecyl sulfate (i.e., tris(hydroxymethyl)aminomethane lauryl sulfate); ursodeoxycholic acid, alkyltrimethylammonium bromide; benzalkonium chloride; benzyldimethylhexadecylammonium chloride; benzyldimethyltetradecylammonium chloride; benzyldodecyldimethylammonium bromide; benzyltrimethylammonium tetrachloroiodate; cetyltrimethylammonium bromide; dimethyldioctadecylammonium bromide; dodecylethyldimethylammonium bromide; dodecyltrimethylammonium bromide; ethylhexadecyldimethylammonium bromide; Girard's reagent T; hexadecyltrimethylammonium bromide; N,N',N'-polyoxyethylene(10)-N-tallow-1,3-diaminopropane; thonzonium bromide; trimethyl(tetradecyl)ammonium bromide, BigCHAP (i.e., N,N-bis[3-(D-gluconamido)propyl] cholamide); bis(polyethylene glycol bis[imidazoyl carbonyl]); polyoxyethylene alcohols, such as Brij® 30 (polyoxyethylene(4) lauryl ether), Brij®35 (polyoxyethylene (23) lauryl ether), Brij® 35P, Brij® 52 (polyoxyethylene 2 cetyl ether), Brij® 56 (polyoxyethylene 10 cetyl ether), Brij® 58 (polyoxyethylene 20 cetyl ether), Brij® 72 (polyoxyethylene 2 stearyl ether), Brij® 76 (polyoxyethylene 10 stearyl ether), Brij® 78 (polyoxyethylene 20 stearyl ether), Brij® 78P, Brij® 92 (polyoxyethylene 2 oleyl ether); Brij® 92V (polyoxyethylene 2 oleyl ether), Brij® 96V, Brij® 97 (polyoxyethylene 10 oleyl ether), Brij® 98 (polyoxyethylene(20) oleyl ether), Brij® 58P, and Brij® 700 (polyoxyethylene (100) stearyl ether); Cremophor® EL (i.e., polyoxyethylenglyceroltriricinoleat 35; polyoxyl 35 castor oil); decaethylene glycol monododecyl ether; decaethylene glycol mono hexadecyl ether; decaethylene glycol mono tridecyl ether; N-decanoyl-N-methylglucamine; n-decyl α-D-glucopyranoside; decyl β-D-maltopyranoside; digitonin; n-dodecanoyl-N-methylglucamide; n-dodecyl α-D-maltoside; n-dodecyl β-D-maltoside; heptaethylene glycol monodecyl ether; heptaethylene glycol monododecyl ether; heptaethylene glycol monotetradecyl ether; n-hexadecyl β-D-maltoside; hexaethylene glycol monododecyl ether; hexaethylene glycol monohexadecyl ether; hexaethylene glycol monooctadecyl ether; hexaethylene glycol monotetradecyl ether; Igepal® CA-630 (i.e., nonylphenyl-polyethylenglykol, (octylphenoxy)polyethoxyethanol, octylphenyl-polyethylene glycol); methyl-6-O—(N-heptylcarbamoyl)-α-D-glucopyranoside; nonaethylene glycol monododecyl ether; N-nonanoyl-N-methylglucamine; octaethylene glycol monodecyl ether; octaethylene glycol monododecyl ether; octaethylene glycol monohexadecyl ether; octaethylene glycol monooctadecyl ether; octaethylene glycol monotetradecyl ether; octyl-β-D-glucopyranoside; pentaethylene glycol monodecyl ether; pentaethylene glycol monododecyl ether; pentaethylene glycol monohexadecyl ether; pentaethylene glycol monohexyl ether; pentaethylene glycol monooctadecyl ether; pentaethylene glycol monooctyl ether; polyethylene glycol diglycidyl ether; polyethylene glycol ether W-1; polyoxyethylene 10 tridecyl ether; polyoxyethylene 100 stearate; polyoxyethylene 20 isohexadecyl ether; polyoxyethylene 20 oleyl ether; polyoxyethylene 40 stearate; polyoxyethylene 50 stearate; polyoxyethylene 8 stearate; polyoxyethylene bis(imidazolyl carbonyl); polyoxyethylene 25 propylene glycol stearate; saponin from quillaja bark; sorbitan fatty acid esters, such as Span® 20 (sorbitan monolaurate), Span® 40 (sorbitane monopalmitate), Span® 60 (sorbitane monostearate), Span® 65 (sorbitane tristearate), Span® 80 (sorbitane monooleate), and Span® 85 (sorbitane trioleate); various alkyl ethers of polyethylene glycols, such as Tergitol® Type 15-S-12, Tergitol® Type 15-S-30, Tergitol® Type 15-S-5, Tergitol® Type 15-S-7, Tergitol® Type 15-S-9, Tergitol® Type NP-10 (nonylphenol ethoxylate), Tergitol® Type NP-4, Tergitol® Type NP-40, Tergitol® Type NP-7, Tergitol® Type NP-9 (nonylphenol polyethylene glycol ether), Tergitol® MIN FOAM Ix, Tergitol® MIN FOAM 2x, Tergitol® Type TMN-10 (polyethylene glycol trimethylnonyl ether), Tergitor Type TMN-6 (polyethylene glycol trimethylnonyl ether), Triton® 770, Triton® CF-10 (benzyl-polyethylene glycol tert-octylphenyl ether), Triton® CF-21, Triton® CF-32, Triton® DF-12, Triton® DF-16, Triton® GR-5M, Triton® N-42, Triton® N-57, Triton® N-60, Triton® N-101 (i.e., polyethylene glycol nonylphenyl ether; polyoxyethylene branched nonylphenyl ether), Triton® QS-15, Triton® QS-44, Triton® RW-75 (i.e., polyethylene glycol 260 mono(hexadecyl/octadecyl) ether and 1-octadecanol), Triton® SP-135, Triton® SP-190, Triton® W-30, Triton® X-15, Triton® X-45 (i.e., polyethylene glycol 4-tert-octylphenyl ether; 4-(1,1,3,3-tetramethylbutyl)phenyl-polyethylene glycol), Triton® X-100 (t-octylphenoxypolyethoxyethanol; polyethylene glycol tert-octylphenyl ether; 4-(1,1,3,3-tetramethylbutyl)phenyl-polyethylene glycol), Triton® X-102, Triton® X-114 (polyethylene glycol tert-octylphenyl ether; (1,1,3,3-tetramethylbutyl) phenyl-polyethylene glycol), Triton® X-165, Triton® X-305, Triton® X-405 (i.e., polyoxyethylene(40) isooctylcyclohexyl ether; polyethylene glycol tert-octylphenyl ether), Triton® X-705-70, Triton® X-151, Triton® X-200, Triton® X-207, Triton® X-301, Triton® XL-80N, and Triton® XQS-20; tetradecyl-β-D-maltoside; tetraethylene glycol monodecyl ether; tetraethylene glycol monododecyl ether; tetraethylene glycol monotetradecyl ether; triethylene glycol monodecyl ether; triethylene glycol monododecyl ether; triethylene glycol monohexadecyl ether; triethylene glycol monooctyl ether; triethylene glycol monotetradecyl ether; polyoxyethylene sorbitan fatty acid esters, such as TWEEN® 20 (polyethylene glycol sorbitan monolaurate), TWEEN® 20 (polyoxyethylene (20) sorbitan monolaurate), TWEEN® 21 (polyoxyethylene (4) sorbitan monolaurate), TWEEN® 40 (polyoxyethylene (20) sorbitan monopalmitate), TWEEN® 60 (polyethylene glycol sorbitan monostearate; polyoxyethylene (20) sorbitan monostearate), TWEEN® 61 (polyoxyethylene (4) sorbitan monostearate), TWEEN® 65 (polyoxyethylene (20) sorbitantristearate), TWEEN® 80 (polyethylene glycol sorbitan monooleate; polyoxyethylene (20) sorbitan monooleate), TWEEN® 81 (polyoxyethylene (5) sorbitan monooleate), and TWEEN® 85 (polyoxyethylene (20) sorbitan trioleate); tyloxapol; n-undecyl β-D-glucopyranoside, CHAPS (i.e., 3-[(3-cholamidopropyl)dimethylammonio]-1-propanesulfonate); CHAPSO (i.e., 3-[(3-cholamidopropyl)dimethylammonio]-2-hydroxy-1-propanesulfonate); N-dodecylmaltoside; α-dodecyl-maltoside; β-dodecyl-maltoside; 3-(decyldimethylammonio) propanesulfonate inner salt (i.e., SB3-10); 3-(dodecyldimethylammonio)propanesulfonate inner salt (i.e., SB3-12); 3-(N,N-dimethyloctadecylammonio)propanesulfonate (i.e., SB3-18); 3-(N,N-dimethyloctylammonio) propanesulfonate inner salt (i.e., SB3-8); 3-(N,N-dimethylpalmitylammonio)propanesulfonate (i.e., SB3-16); MEGA-8; MEGA-9; MEGA-10; methylheptylcarbamoyl glucopyranoside; N-nonanoyl N-methylglucamine; octyl-glucopyranoside; octyl-thioglucopyranoside; octyl-β-thio-glucopyranoside; 3-[N,N-dimethyl(3-myristoylaminopropyl)ammonio]propanesulfonate (i.e., ASB-14); and deoxycholatic acid, and various combinations thereof.

In another embodiment, the detergent composition of the invention may optionally include a lytic enzyme. A wide variety of enzymes may be used herein. Exemplary enzymes include beta glucurondiase; glucanase; glusulase; lysozyme; lyticase; mannanase; mutanolysin; zymolyase, cellulase, chitinase, lysostaphin, pectolyse, streptolysin O, and various combinations thereof. See, e.g., Wolska-Mitaszko, et al., Analytical Biochem., 116:241-47 (1981); Wiseman, Process Biochem., 63-65 (1969); and Andrews & Asenjo, Trends in Biotech., 5:273-77 (1987).

As will readily be appreciated by a skilled artisan, the type of cell being lysed may affect the choice of enzyme. See Coakley, et al., Adv. Microb. Physiol., 16:279-341 (1977). For example, with regards to proteins or peptides, chitinase, beta glucuronidase, mannanase, and pectolyse are all useful when the host cell is a plant cell. Yeast cells are difficult to disrupt because the cell walls may form capsules or resistant spores. DNA can be extracted from yeast by using lysing enzymes such as lyticase, chitinase, zymolase, and gluculase to induce partial spheroplast formation; spheroplast are subsequently lysed to release DNA. Lyticase is preferred to digest cell walls of yeast and generate spheroplasts from fungi for transformation. Lyticase hydrolyzes poly($\beta$-1,3-glucose) such as yeast cell-wall glucan.

Lysozyme and mutanolysin are useful when the host cell is a bacterial cell. Lysozyme hydrolyzes the beta 1-4 glycosidic bond between N-acetylglucosamine and N-acetylmuramic acid in the polysaccharide backbone of peptidoglycan. It is effective in lysing bacteria by hydrolyzing the peptidoglycan that is present in bacterial cell walls.

In yet another embodiment, the detergent composition also may include a chaotrope. In some instances chaotropes alone are sufficient to lyse the host cell. In particular, chaotropes are used when the cellular component is RNA. Examples of chaotropes that may be used herein include urea, guanidine HCl, guanidine thiocyanate, guanidium thiosulfate, and thiourea.

A further embodiment of the invention encompasses the use of one or more buffers to control pH, an anti-foaming agent to prevent excessive foaming or frothing, a bulking agent, enzymatic inhibitors, and other processing enzymes that may aid in the purification of the cellular component. Exemplary buffers include TRIS, TRIS-HCl, HEPES, and phosphate. Exemplary anti-foaming agents include Antifoam 204; Antifoam A Concentrate; Antifoam A Emulsion; Antifoam B Emulsion; and Antifoam C Emulsion. Exemplary bulking agents include sodium chloride, potassium chloride, and polyvinylpyrrolidone (PVP). Suitable processing enzymes and enzymatic inhibitors include nucleases, such as Benzonase® endonuclease; DNAse (e.g., Dnase I); RNAse (e.g., Rnase A); proteases, such as proteinase K; nuclease inhibitors; protease inhibitors, such as phosphoramidon, pepstatin A, bestatin, E-64, aprotinin, leupeptin, 1,10-phenanthroline, antipain, benzamidine HCl, chymostatin, EDTA, e-aminocaproic acid, trypsin inhibitor, and 4-(2-aminoethyl) benzenesulfonyl fluoride hydrochloride; and phosphatase inhibitors, such as cantharidin, bromotetramisole, microcystin LR, sodium orthovanadate, sodium molybdate, sodium tartrate, and imidazole; among others.

Like lysing enzymes, the choice of processing enzyme and enzymatic inhibitor will also vary depending on several factors, including the type of material to be extracted (e.g., peptides, proteins, nucleic acids, etc.), as well as the type of cell to be lysed (e.g., plant, yeast, bacterial, fungal, mammalian, insect, etc.). For example, nucleases hydrolyze or degrade nucleic acids. As will be appreciated by the skilled artisan, it would be desirable for the detergent composition of the invention to comprise a nuclease when the target product is a protein or peptide, but not when the target product is a nucleic acid. Likewise, proteases break down or degrade proteins. It would thus be desirable for the detergent composition to comprise a protease when the target product is a nucleic acid, but not when the target product is a peptide or protein. Similar reasoning may be applied when selecting other enzymes or inhibitors. Thus, in general, enzymes or inhibitors such as proteases, nuclease inhibitors, and lysozymes are useful when the target product is a nucleic acid. Other enzymes or inhibitors, such as Benzonase® endonuclease, protease inhibitors, phosphatase inhibitors, DNase, RNase, or other nucleases are useful when the target product is a protein or peptide. With regards to nucleic acids, Rnase A could be used for the extraction of bacterial and mammalian DNA. Dnase I may be used for the extraction of bacterial RNA, yeast RNA, RNA from animal cells and tissues, and RNA from biological fluids. A protease, such as proteinase K, may be used to extract DNA from all cell types.

By way of example, when the target product is a protein or peptide, the detergent composition of the invention may additionally include lysozymes, nucleases, Benzonase® endonuclease, buffers, protease inhibitors, phosphatase inhibitors, or chaotropic reagents, or various combinations thereof.

In another embodiment, when the target product is DNA, the detergent composition of the invention may additionally include lysozymes, nuclease inhibitors, RNase, buffers, or proteases, or various combinations thereof.

In still another embodiment, when the target product is RNA, the detergent composition of the invention may preferably include, chaotropic reagents, or buffers, or various combinations thereof. Enzymes would not be typically used in this application since the chaotrope will inactivate them.

In one embodiment, the composition will include any of the detergent compositions detailed in either of Table A or Table B, lysozyme, Tris-HCl, and Dnase I.

In another embodiment, the composition will include any of the detergent compositions detailed in either of Table A or Table B, protease inhibitors, lysozyme, and Benzonase® endonuclease.

In still another embodiment, the composition will include 3-(N,N-Dimethyltetradecylammonio)propanesulfonate and 3-(4-Heptyl)phenyl-3-hydroxypropyl)dimethylammoniopropanesulfonate and Tris-HCl.

In yet another embodiment, the composition will include 3-(N,N-Dimethyltetradecylammonio)propanesulfonate and 3-(4-Heptyl)phenyl-3-hydroxypropyl)dimethylammoniopropanesulfonate and a phosphate buffer.

The amount of the detergent and the relative proportions of each component in the composition can and will vary depending upon the type of host cell, the class of detergent compositions selected and the degree of cell permeation desired in a defined period of time. Thus, in one embodiment, the concentration of any single detergent is from about 0.01% to about 5% (w/v), preferably from about 0.05% to about 4% (w/v), more preferably from about 0.1% to about 4% (w/v), and even more preferably from about 0.1% to about 2%. By way of example, when the detergent composition comprises 3-(N,N-Dimethyltetradecylammonio)propanesulfonate and 3-(4-Heptyl)phenyl-3-hydroxypropyl)dimethylammoniopropanesulfonate, the concentration of 3-(N,N-Dimethyltetradecylammonio)propanesulfonate may range from about 0.5% to about 2% (w/v) and the concentration of 3-(4-Heptyl) phenyl-3-hydroxypropyl)dimethylammoniopropanesulfonate may range from about 0.01 to about 1% (w/v). In an even more typical embodiment, when the detergent composition comprises 3-(N,N-Dimethyltetradecylammonio)propanesulfonate and 3-(4-Heptyl)phenyl-3-hydroxypropyl) dimethylammoniopropanesulfonate, the concentration of 3-(N,N-Dimethyltetradecylammonio)propanesulfonate may range from about 0.5% to about 1% (w/v) and the concentration of 3-(4-Heptyl)phenyl-3-hydroxypropyl)dimethylammoniopropanesulfonate may range from about 0.01 to about 0.2% (w/v). Stated another way, when the detergent composition comprises 3-(N,N-Dimethyltetradecylammonio)propanesulfonate and 3-(4-Heptyl)phenyl-3-hydroxypropyl) dimethylammoniopropanesulfonate, the ratio of 3-(N,N-Dimethyltetradecylammonio)propanesulfonate to of 3-(4-Heptyl)phenyl-3-hydroxypropyl) dimethylammoniopropanesulfonate may range from about 20:1 to about 1:1 (w/v), but is more typically 10:1 (w/v).

In another embodiment, the concentration of each lytic enzyme is from about 0.01 mg/ml to about 0.2 mg/ml. In yet another embodiment, the concentration of buffer is such that the pH of the cellular solution is maintained at about pH 3 to about pH 12, for the duration of the period of time during which extraction or extraction and isolation occurs. In another embodiment, the concentration of protease inhibitor is from about 10 nM to about 10 mM. In another embodiment, the concentration of phosphatase inhibitor is from about 0.01 nM to about 10 mM.

Applications

The detergent compositions described herein may be used in a number of suitable applications, some of which are described more fully below. Briefly, in one such application the composition may be used solely for the purpose of extraction. In this application, the composition is employed to release at least some of the target product from the host cell in which it is expressed by causing partial or complete cell lysis. In one alternative of this embodiment, for example, the detergent composition may be utilized to lyse a pellet comprising bacterial cells expressing a target product, such as a recombinant protein. Typically in this embodiment, the bacterial cells are grown in accordance with methods generally known in the art and the cells are then harvested by a suitable method, such as centrifugation. After centrifugation, the bacterial cell fraction will comprise a pellet. The detergent composition of the invention may be added to the bacterial pellet expressing the recombinant protein at the concentration described above, or typically at a ratio of about 1 to about 30 mL/gram of pellet, and more typically from a ratio of about 5 to about 20 mL/gram of pellet. The bacterial pellet and detergent composition are then typically incubated with mixing for a suitable period of time, such as for about 10 to about 30 minutes at room temperature. The solution may then be clarified by centrifugation, and the soluble fraction, which contains soluble proteins from the cell lysate (i.e., the target product), may then be further analyzed via a number of methods known in the art, including SDS-PAGE, enzymatic assay, or protein concentration analysis. In additional embodiments, the target product may be further purified from the soluble fraction by any method generally known in the art or has more fully described below.

In yet another embodiment, the detergent composition of the invention may be employed for in-media lysis. Briefly in one alternative of this embodiment, bacterial cells expressing a target product are grown in accordance with any method generally known in the art. The detergent composition is then added at an appropriate concentration, as described above, directly to the liquid culture media without first harvesting the cells. The solution (i.e., detergent composition and liquid culture media containing the bacterial cells) is then mixed and incubated for a suitable period of time, such as for about 10 to about 30 minutes at room temperature. The whole culture extract, which contains soluble proteins from the cell lysate (i.e., the target product), may then be further analyzed via a number of methods known in the art, including SDS-PAGE, enzymatic assay, or protein concentration analysis. In additional embodiments, the target product may be further purified from the whole culture extract by any method generally known in art or has more fully described below.

In certain embodiments it may be highly desirable to minimize the number of steps required for extraction or extraction and isolation, especially in high throughput applications. Toward that end, in an exemplary embodiment, any of the detergent compositions detailed above, or detergent compositions and capture ligands (as detailed below) may be adsorbed to a container for use in a one step extraction or extraction and isolation process. Embodiments employing containers comprising either a detergent composition or a detergent composition and capture ligand are described in more detail below.

Containers For Use in Extraction or Extraction and Isolation of Target Products

One aspect of the invention, therefore, encompasses a container that may be adsorbed or coated with suitable reagents for either extraction or extraction and isolation of a target product from a host cell. In general, the container of the present invention is a well suitable for holding a liquid, the well comprising a bottom, a mouth, and a sidewall formation. In one embodiment, the sidewall formation may have any of a variety of geometric shapes; for example, in this embodiment, the sidewall formation may be cylindrical, polygonal, conical, or concave (e.g., hemispherical). Similarly, in one embodiment, the bottom has any of a variety of geometric shapes; for example, in this embodiment, the bottom may be flat, curved or even comprise a single point (e.g., the lower most point of an inverted cone). The mouth serves as an opening through which a liquid may be introduced to the well; in one embodiment, the mouth and the bottom are at opposite ends of the sidewall formation with the mouth being defined by the opening at the top of the sidewall formation. In its various embodiments, therefore, the container may be a cylinder, flask, jar, beaker, vial, bottle, column, or even a depression in a surface. In addition, the container may be presented as a single, freestanding, receptacle or it may be one of a plurality of physically integrated receptacles. In one embodiment, therefore, the container is a well of a unitary multiwell plate such as a 48 well, 96 well, 384 well, 1536 well, etc., multiwell plate. Also, the container may have a permanently closed bottom or the bottom may comprise a valved or capped opening through which liquid in the container may optionally be removed.

Containers used for the extraction or the extraction and affinity capture of peptides, protein, nucleic acids, or other cellular components may be of a variety of dimensions, and need not contain large volumes of liquids. In general, the container will hold a volume of less than 50 L. In one embodiment, the container will hold a volume of no more than 1 L, but no less than 1.0 µl. In another embodiment, the container will hold a volume of from about 10 µl to about 100 ml.

The interior surface of the container, which comprises the sidewall formation and bottom, defines the liquid volume capacity of the container. In one embodiment, the ratio of the surface area to the volume defined by the interior surface of the container is less than about 4 $mm^2/\mu l$. In another embodiment, the surface area to volume ratio defined by the interior surface of the container does not exceed about 3 $mm^2/\mu l$. In another embodiment, the surface area to volume ratio defined by the interior surface of the container does not exceed about 2 $mm^2/\mu l$. In another embodiment, the surface area to volume ratio defined by the interior surface of the container does not exceed about 1 $mm^2/\mu l$.

Depending upon the intended use and operator preferences, the containers may optionally be sealed. In one embodiment, therefore, the container comprises a lid or cap that fits over the mouth to isolate the contents of the container from the surrounding ambient. In another embodiment, the mouth of the container is open to the environment. Thus, for example, when the container is in the format of a multiwell plate, (i) each well may be individually sealed by a separate lid (e.g., a plastic cover wrapping), (ii) a fraction or a plurality of wells may be sealed by a common lid, leaving the remaining fraction of wells open to the surrounding ambient, (iii) all of the wells may be sealed by a common lid, or (iv) all of the wells may be open to the surrounding ambient. In addition, the lid may comprise a single port for the introduction of liquid into the container or it may comprise a plurality of ports for the introduction or introduction and removal of liquid from the container. In another embodiment, when the bottom of the container comprises an opening through which liquid in the container may optionally be removed, the mouth and bottom of the container may both optionally be capped.

In general, the container may be formed from a variety of natural or synthetic materials. For example, the container may be plastic, silica, glass, metal, ceramic, magnetite, polyesters, polystyrene, polypropylene, polyethylene, nylon, polyacrylamide, cellulose, nitrocellulose, latex, etc.

Containers Comprising Detergent Compositions

To aid in the extraction or extraction and isolation of a cellular component, such as a peptide, protein, or nucleic acid, from a host cell, the containers of the present invention comprise any of the detergent compositions detailed above. In one embodiment, the composition is in a concentration that causes the membrane of the host cell to rupture and release its contents into a solution containing the detergent composition. In another embodiment, the detergent composition merely renders the membrane sufficiently permeable to release some, but not necessarily all of its cellular components.

The detergent composition may be provided within the container by a variety of manners. In one embodiment, the detergent composition is adsorbed (as a dry composition) to the interior surface of the container (or, alternatively, to a polymeric coating overlying the container surface, if present). In one such embodiment, for example, the detergent composition is adsorbed to at least a portion of the sidewall formation of the container. In another embodiment, the detergent composition is adsorbed to at least a portion of the bottom of the container. In another embodiment, the detergent composition is adsorbed to at least a portion of each of the bottom and the sidewall formation of the container. Optionally, if the container comprises a polymer matrix, the detergent composition may be adsorbed to at least a portion of the surface of the polymer matrix. In another embodiment, the detergent composition is adsorbed to another body, for example, a support such as a bead, rod, mesh (such as a filter) or other porous body which is loosely contained within the volume of the container or affixed to the interior surface of the container. Such supports as well as the container itself may be comprised of, for example, polystyrene, polypropylene, polyethylene, glass, nylon, polyacrylamides, celluloses, nitrocellulose, other plastic polymers, metals, magnetite, or other synthetic substances. In another embodiment, the detergent composition is adsorbed to at least a portion of the interior surface of the container and to a body, for example, a support such as a bead, rod, mesh (such as a filter) or other porous body which is loosely contained within the volume of the container or affixed to the interior surface of the container.

The ratio of the surface area of the surfaces coated with detergent composition (i.e., the sum of the surface area of the coated interior surface and/or coated bodies contained within the volume of the container) to the volume of the container may be controlled in accordance with one aspect of the present invention. In one embodiment, the surface area to volume ratio, SA:V, wherein SA is the surface area of the coated interior surface of the container and the surface of any coated bodies contained with the volume of the container and V is the volume of the container, is less than about 4 $mm^2/\mu l$. In another embodiment, this surface area to volume ratio does not exceed about 3 $mm^2/\mu l$. In another embodiment, this surface area to volume ratio does not exceed about 2 $mm^2/\mu l$. In another embodiment, this surface area to volume ratio does not exceed about 1 $mm^2/\mu l$.

The coating of the detergent composition on the interior surface of the container and/or bodies contained within the volume of the container will typically be adsorbed as a dry material, e.g., a composition having a moisture content of not more than about 5 wt. %. Alternatively, the detergent composition may be provided in the form of a gel or paste, i.e., a material that has a viscosity of greater than about 10,000 centipoise, coated on the interior surface or a portion of the interior surface of the container, or additionally on included bodies.

In one alternative embodiment, the detergent composition is provided to and resides within the container as a free-flowing powder, granule, or tablet(s) rather than as an adsorbed layer on the interior surface of the container or bodies contained within the volume of the container. In general, finer particles tend to dissolve more rapidly than larger particles. To minimize the risk of loss and/or contamination of the detergent composition, it may be preferred to provide a lid over the mouth of the container.

In another alternative embodiment, the detergent composition may be present in the container as a dissolved or slurried component. To avoid undesired dilution of any solutions or suspensions containing the host cell, in this embodiment the liquid in which the detergent composition is dissolved or slurried preferably contains a high concentration of the detergent composition, e.g., greater than about 10% by weight. In another embodiment, the concentration of the detergent composition is greater than about 20% by weight. Again, to minimize the risk of loss and/or contamination of the detergent composition, it may be preferred to cover the container with a lid.

Regardless of whether the detergent composition is present in the container as an adsorbed, free-flowing, dissolved or slurried component, when a solution or suspension containing a host cell is added to the container, the detergent composition will be dissolved or diluted by the suspension containing the host cell, and the host cell is lysed. If the detergent composition contains all reagents needed for lysis, there is no need to perform multiple pipetting steps to ensure all the needed detergent compositions are present. Furthermore, as noted above, the detergent composition need not completely solubilize the host cell to be effective. Rather, the host cell need only be lysed to the extent necessary to release some or all of the target product into solution. In addition, the detergent composition need not lyse all host cells in any particular cellular suspension to be effective, so long as some of the host cells are lysed.

Containers Comprising Capture Ligands

In one aspect of the invention, once the host cell has been lysed with the detergent combinations of the invention, the cellular components may be isolated and separated from other cellular debris through the use of a capture ligand immobilized on a support material in the container. Suitable containers (described above) and methods for coating the containers with reagents is described in detail below. The capture ligand may be supported directly or indirectly by the interior surface of the container or by a bead or other support which is placed in, affixed to, or otherwise held in the container. In one embodiment, the capture ligand is positioned on the bottom of the container. In another embodiment, the capture ligand is positioned on a sidewall formation. In another embodiment, the capture ligand is positioned on both the bottom and the sidewall formation of a container. In another embodiment, the supported capture ligand is positioned in the container at a location which allows the capture ligand to be exposed to intact host cells or solid cellular components derived therefrom which may be present in the container.

Advantageously, the reagents, components and methods of the present invention permit a range of capture ligands to be used. In one preferred embodiment, the capture ligands are capable of isolating the cellular component in a liquid suspension comprising cellular debris.

A variety of techniques for purifying proteins, peptides, DNA, RNA, or other cellular components are well known in the art, and can be used in conjunction with the containers and processes described herein. See, e.g., Becker, et al., Biotech. Advs., 1:247-61 (1983). In one embodiment, any capture method may be used, so long as the presence of the detergent composition does not interfere with binding. For example, a common method of protein purification involves the production of a fusion protein comprising the target protein and an affinity tag capable of binding with high specificity to an affinity matrix. Thus, in one aspect, the containers of the present invention comprise a supported capture ligand capable of binding with high specificity the affinity tag of the target protein or peptide, thus resulting in isolation of the target protein or peptide from other proteins and cellular debris. In some instances, the target protein or peptide naturally contains a sequence capable of binding to a corresponding capture ligand. In this instance, the protein need not be recombinant, so long as there is a capture ligand capable of binding the target protein or peptide. Some specific examples of well known affinity capture systems that can be used to capture proteins or peptides include (i) metal chelate chromatography (e.g., nickel or cobalt interactions with histidine tags), (ii) immunogenic capture systems, such as those using antigen-antibody interactions (e.g., the FLAG® peptide, c-myc tags, HA tags, etc.), (iii) a glutatione-S-transferase (GST) capture system, and (iv) the biotin-avidin/streptavidin capture system. Other techniques include ion exchange chromatography, including both anion and cation exchange, as well as hydrophobic chromatography, and thiophilic chromatography. Combinations of these various capture methods may also be used, such as with mixed mode chromatography. These techniques are a few of the techniques commonly used to purify proteins. Hydrophobic chromatography, ion exchange chromatography, and various hybridization techniques, for example, utilizing nucleotide sequences with specificity for the target DNA or RNA, are also commonly used to purify DNA and RNA. Another common RNA capture method is poly (dT). Since these and other capture systems are well known in the art, they will only be described briefly herein.

Immobilized metal affinity chromatography ("IMAC") uses the affinity of certain residues within proteins for metal ions, to purify proteins. In IMAC, metal ions are immobilized onto to a solid support, and used to capture proteins comprising a metal chelating peptide. The metal chelating peptide may occur naturally in the protein, or the protein may be a recombinant protein with an affinity tag comprising a metal chelating peptide. Some of the most commonly used metal ions include nickel ($Ni^{2+}$), zinc ($Zn^{2+}$), copper ($Cu^{2+}$), iron ($Fe^{3+}$), cobalt ($Co^{2+}$), calcium ($Ca^{2+}$), aluminum ($Al^{3+}$), magnesium ($Mg^{2+}$), manganese ($Mn^{2+}$), and gallium ($Ga^{3+}$). Thus, in one embodiment, the container and/or support comprises metal ions immobilized upon its surface, or a portion thereof, wherein the metal ions are selected from the group consisting of nickel ($Ni^{2+}$), zinc ($Zn^{2+}$), copper ($Cu^{2+}$), iron ($Fe^{3+}$), cobalt ($Co^{2+}$), calcium ($Ca^{2+}$), aluminum ($Al^{3+}$), magnesium ($Mg^{2+}$), manganese ($Mn^{2+}$), and gallium ($Ga^{3+}$). Preferably, the metal ion is nickel, copper, cobalt, or zinc. Most preferably, the metal ion is nickel.

A variety of proteins that contain a metal chelating peptide may be purified in this way. In one embodiment, the metal chelating peptide may have the formula His-X, wherein X is selected from the group consisting of Gly, His, Tyr, Trp, Val, Leu, Ser, Lys, Phe, Met, Ala, Glu, Ile, Thr, Asp, Asn, Gln, Arg, Cys, and Pro, as described more fully in Smith, et al. (1986) U.S. Pat. No. 4,569,794, incorporated herein by reference. The metal chelating peptide may also have the formula $(His-X)_n$, wherein X is selected from the group consisting of Asp, Pro, Glu, Ala, Gly, Val, Ser, Leu, Ile, or Thr, and n is 3 to 6, as described more fully in Sharma, et al. (1997) U.S. Pat. No. 5,594,115, incorporated herein by reference. In another embodiment, the metal chelating peptide includes a poly(His) tag of the formula $(His)_y$, wherein y is at least 2-6, as described more fully in Dobeli, et al. (1994) U.S. Pat. No. 5,310,663, incorporated herein by reference. Other examples of metal chelating peptides will be known to those in the art.

In one embodiment, the capture ligand is a metal chelate as described in WO 01/81365. More specifically, in this embodiment the capture ligand is a metal chelate derived from metal chelating composition (1):

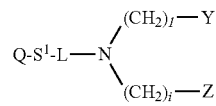

wherein, Q is a carrier; $S^1$ is a spacer; L is -A-T-CH(X)— or —C(=O)—; A is an ether, thioether, selenoether, or amide linkage; T is a bond or substituted or unsubstituted alkyl or alkenyl; X is —$(CH_2)_kCH_3$, —$(CH_2)_kCOOH$, —$(CH_2)_kSO_3H$, —$(CH_2)_kPO_3H_2$, —$(CH_2)_kN(J)_2$, or —$(CH_2)_kP(J)_2$, preferably —$(CH_2)_kCOOH$ or —$(CH_2)_kSO_3H$; k is an integer from 0 to 2; J is hydrocarbyl or substituted hydrocarbyl; Y is —COOH, —H, —$SO_3H$, —$PO_3H_2$, —$N(J)_2$, or —$P(J)_2$, preferably, —COOH; Z is —COOH, —H, —$SO_3H$, —$PO_3H_2$, —$N(J)_2$, or —$P(J)_2$, preferably, —COOH; and i is an integer from 0 to 4, preferably 1 or 2.

In general, the carrier, Q, may comprise any solid or soluble material or compound capable of being derivatized for coupling. Solid (or insoluble) carriers may be selected from a group including agarose, cellulose, methacrylate co-polymers, polystyrene, polypropylene, paper, polyamide, polyacrylonitrile, polyvinylidene, polysulfone, nitrocellulose, polyester, polyethylene, silica, glass, latex, plastic, gold, iron oxide and polyacrylamide, but may be any insoluble or solid compound able to be derivatized to allow coupling of the remainder of the composition to the carrier, Q. Soluble carriers include proteins, nucleic acids including DNA, RNA, and oligonucleotides, lipids, liposomes, synthetic soluble polymers, proteins, polyamino acids, albumin, antibodies, enzymes, streptavidin, peptides, hormones, chromogenic dyes, fluorescent dyes, flurochromes or any other detection molecule, drugs, small organic compounds, polysaccharides and any other soluble compound able to be derivatized for coupling the remainder of the composition to the carrier, Q. In one embodiment, the carrier, Q, is the container of the present invention. In another embodiment, the carrier, Q, is a body provided within the container of the present invention.

The spacer, $S^1$, which flanks the carrier comprises a chain of atoms which may be saturated or unsaturated, substituted or unsubstituted, linear or cyclic, or straight or branched. Typically, the chain of atoms defining the spacer, $S^1$, will consist of no more than about 25 atoms; stated another way, the backbone of the spacer will consist of no more than about 25 atoms. More preferably, the chain of atoms defining the spacer, $S^1$, will consist of no more than about 15 atoms, and still more preferably no more than about 12 atoms. The chain of atoms defining the spacer, $S^1$, will typically be selected from the group consisting of carbon, oxygen, nitrogen, sulfur, selenium, silicon and phosphorous and preferably from the group consisting of carbon, oxygen, nitrogen, sulfur and selenium. In addition, the chain atoms may be substituted or unsubstituted with atoms other than hydrogen such as hydroxy, keto (═O), or acyl such as acetyl. Thus, the chain may optionally include one or more ether, thioether, selenoether, amide, or amine linkages between hydrocarbyl or substituted hydrocarbyl regions. Exemplary spacers, $S^1$, include methylene, alkyleneoxy (—$(CH_2)_aO$—), alkylenethioether (($CH_2)_aS$—), alkyleneselenoether (—$(CH_2)_aSe$—), alkyleneamide (($CH_2)_aNR^1C$(═O)—), alkylenecarbonyl (($CH_2)_aC$(═O)—), and combinations thereof wherein a is generally from 1 to about 20 and $R^1$ is hydrogen or hydrocarbyl, preferably alkyl. In one embodiment, the spacer, $S^1$, is a hydrophilic, neutral structure and does not contain any amine linkages or substituents or other linkages or substituents which could become electrically charged during the purification of a polypeptide.

As noted above, the linker, L, may be -A-T-CH(X)— or —C(═O)—. When L is -A-T-CH(X)—, the chelating composition corresponds to the formula:

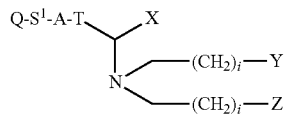

wherein, Q, $S^1$, A, T, X, Y, and Z are as previously defined. In this embodiment, the ether (—O—), thioether (—S—), selenoether (—Se—) or amide (—$NR^1C$(═O)—) or (—C(═O)$NR^1$—) wherein $R^1$ is hydrogen or hydrocarbyl) linkage is separated from the chelating portion of the molecule by a substituted or unsubstituted alkyl or alkenyl region. If other than a bond, T is preferably substituted or unsubstituted $C_1$ to $C_6$ alkyl or substituted or unsubstituted $C_2$ to $C_6$ alkenyl. More preferably, A is —S—, T is —$(CH_2)_n$—, and n is an integer from 0 to 6, typically 0 to 4, and more typically 0, 1 or 2. When L is —C(═O)—, the chelating composition corresponds to the formula:

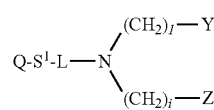

wherein, Q, $S^1$, i, Y, and Z are as previously defined.

In a preferred embodiment, the sequence —$S^1$-L-, in combination, is a chain of no more than about 35 atoms selected from the group consisting of carbon, oxygen, sulfur, selenium, nitrogen, silicon and phosphorous, more preferably only carbon, oxygen sulfur and nitrogen, and still more preferably only carbon, oxygen and sulfur. To reduce the prospects for non-specific binding, nitrogen, when present, is preferably in the form of an amide moiety. In addition, if the carbon chain atoms are substituted with anything other than hydrogen, they are preferably substituted with hydroxy or keto. In a preferred embodiment, L comprises a portion (sometimes referred to as a fragment or residue) derived from an amino acid such as cystine, homocystine, cysteine, homocysteine, aspartic acid, cysteic acid or an ester thereof such as the methyl or ethyl ester thereof.

Exemplary chelating compositions include any of the compounds delineated in Table C.

TABLE C

| Compound No. | Structure* |
|---|---|
| 1-3 | 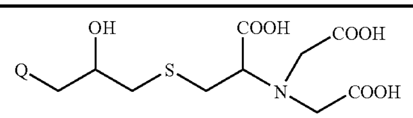 |
| 1-4 | 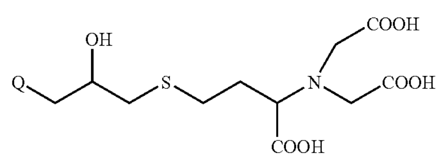 |
| 1-5 | 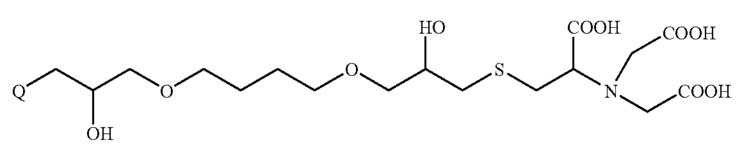 |
| 1-6 | 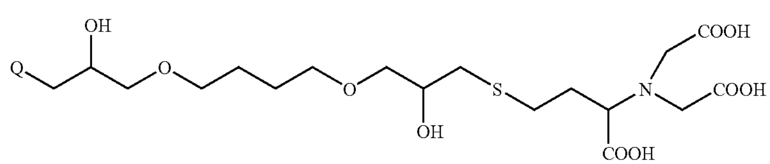 |
| 1-7 | 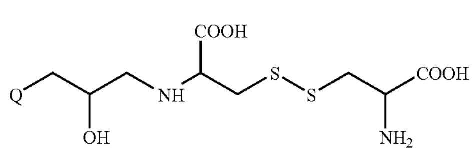 |

TABLE C-continued

| Compound No. | Structure* |
|---|---|
| 1-8 | 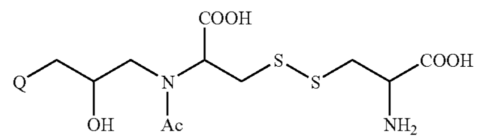 |
| 1-9 | 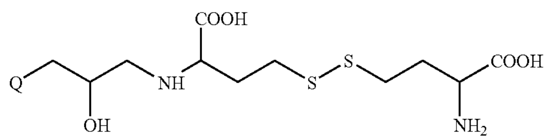 |
| 1-10 | 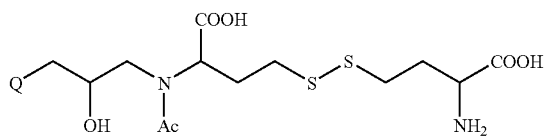 |
| 1-11 | 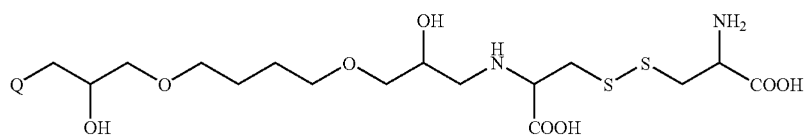 |
| 1-12 | 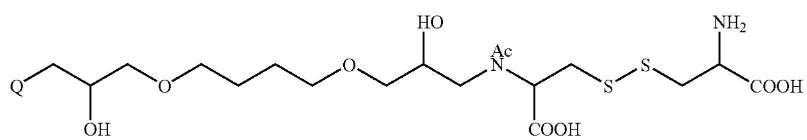 |
| 1-13 | 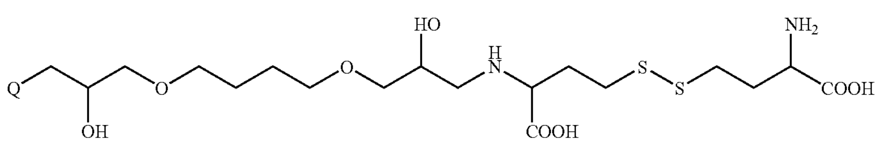 |
| 1-14 | 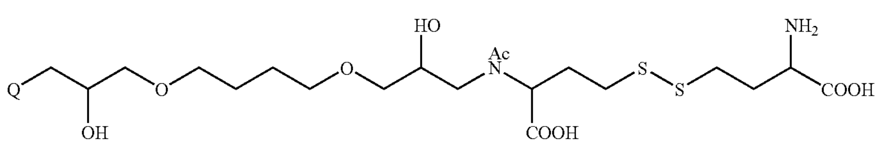 |
| 1-15 | 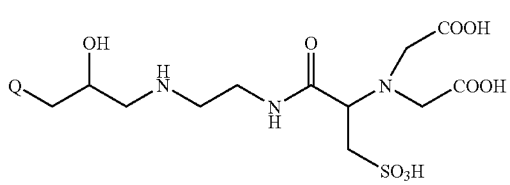 |
| 1-16 | 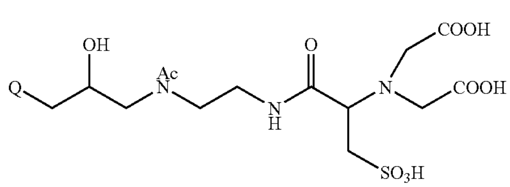 |
| 1-17 | 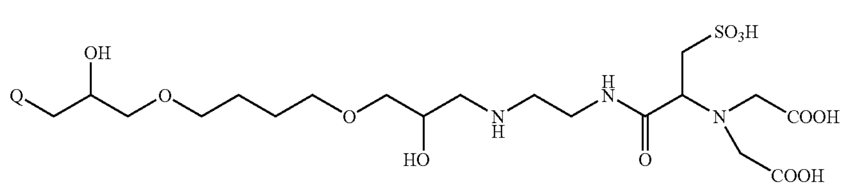 |

TABLE C-continued

| Compound No. | Structure* |
|---|---|
| 1-18 | 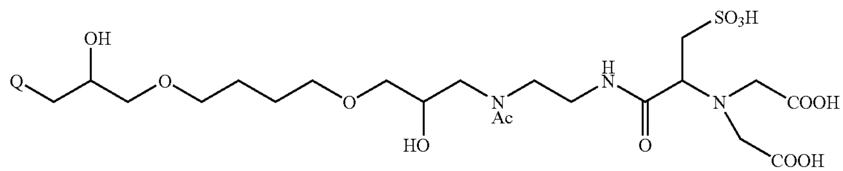 |
| 1-19 | 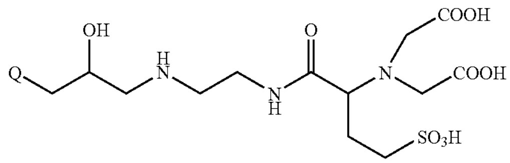 |
| 1-20 | 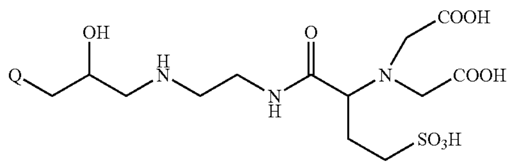 |
| 1-21 | 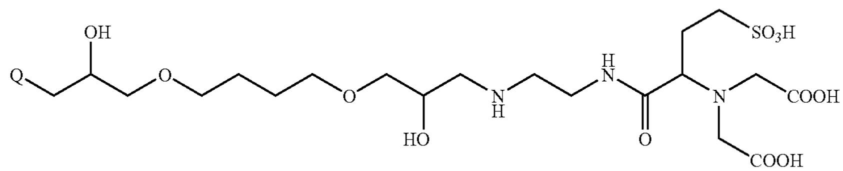 |
| 1-22 | 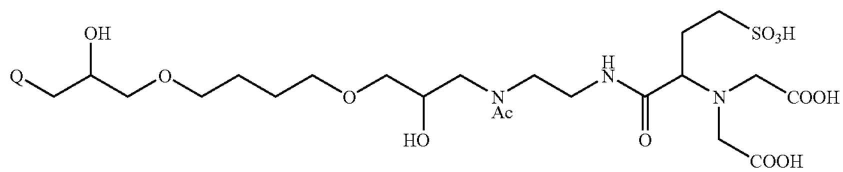 |
| 1-23 | 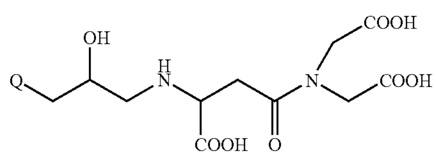 |
| 1-24 | 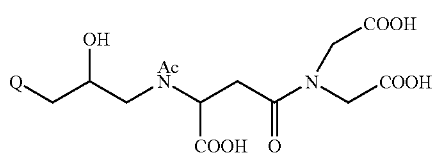 |
| 1-25 | 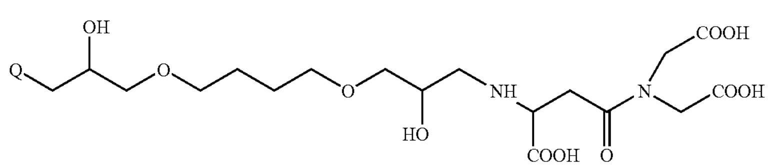 |
| 1-26 | 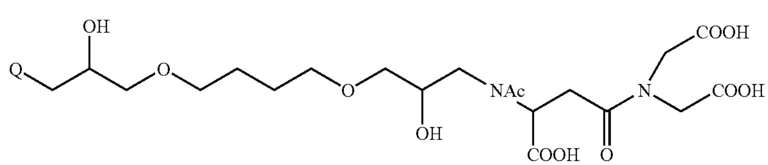 |

*Q is a carrier and Ac is acetyl.

In a further exemplary embodiment, the capture ligand is a metal chelate having the formula:

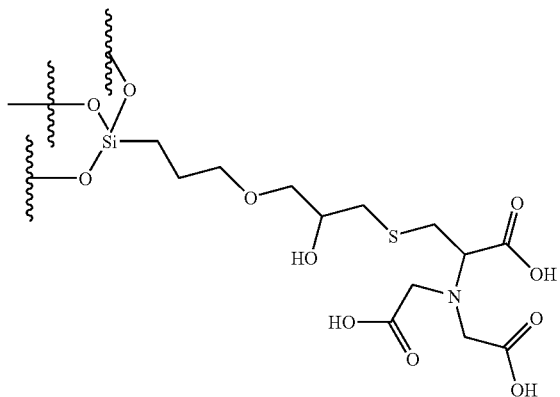

In another embodiment, the capture ligand, is a metal chelate of the type described in U.S. Pat. No. 5,047,513. More specifically, in this embodiment the capture ligand is a metal chelate derived from nitrilotriacetic acid derivatives of the formula:

$$NH_2—(CH_2)_x—CH(COOH)—N(CH_2COOH)_2$$

wherein x is 2, 3 or 4. In this embodiment, the nitrilotriacetic acid derivative is immobilized on any of the previously described carriers, Q.

In these embodiments in which the capture ligand is a metal chelate as described in WO 01/81365 or U.S. Pat. No. 5,047,513, the metal chelate preferably contains a metal ion selected from among nickel ($Ni^{2+}$), zinc ($Zn^{2+}$), copper ($Cu^{2+}$), iron ($Fe^{3+}$), cobalt ($Co^{2+}$), calcium ($Ca^{2+}$), aluminum ($Al^{3+}$), magnesium ($Mg^{2+}$), and manganese ($Mn^{2+}$). In a particularly preferred embodiment, the metal chelate comprises nickel ($Ni^{2+}$).

Another common purification technique that can be used in the context of the present invention is the use of an immunogenic capture system. In such systems, an epitope tag on a protein or peptide allows the protein to which it is attached to be purified based upon the affinity of the epitope tag for a corresponding ligand (e.g., antibody) immobilized on a support. One example of such a tag is the sequence Asp-Tyr-Lys-Asp-Asp-Asp-Asp-Lys, or DYKDDDDK (SEQ. ID. NO. 1); antibodies having specificity for this sequence are sold by Sigma-Aldrich Co. (St. Louis, Mo.) under the FLAG® trademark. Another example of such a tag is the sequence Asp-Leu-Tyr-Asp-Asp-Asp-Asp-Lys, or DLYDDDDK (SEQ. ID. NO. 2); antibodies having specificity for this sequence are sold by Invitrogen (Carlsbad, Calif.). Another example of such a tag is the 3× FLAG® sequence Met-Asp-Tyr-Lys-Asp-H is -Asp-Gly-Asp-Tyr-Lys-Asp-H is -Asp-Ile-Asp-Tyr-Lys-Asp-Asp-Asp-Asp-Lys (SEQ. ID. NO. 3); antibodies having specificity for this sequence are sold by Sigma-Aldrich Co. (St. Louis, Mo.). Thus, in one embodiment, the container comprises immobilized antibodies that have specificity for SEQ. ID. NO. 1; in another embodiment, the container comprises immobilized antibodies which have specificity for SEQ. ID. NO. 2. In another embodiment, the container comprises immobilized antibodies that have specificity for SEQ. ID. NO. 3. For example, in one embodiment, an ANTI-FLAG® M1, M2, or M5 antibody, sold by Sigma-Aldrich Co. (St. Louis, Mo.), is immobilized on the interior surface of the container, or a portion thereof, and/or a bead or other support within the container.

Other tags may also be used to purify recombinant proteins based on their affinity for a corresponding ligand attached to a substrate. Some examples of such other tags include c-myc, maltose binding protein (MBP), influenza A virus hemagglutinin (HA), and β-galactosidase, among others. By attaching the corresponding ligand to the containers and/or solid supports of the present invention, recombinant proteins containing these affinity tags may be purified from other proteins and cellular debris, as described herein. Non-recombinant proteins may be purified in a similar manner, by attaching a ligand with affinity for the protein or peptide sequence, or a part of that sequence, to the containers and/or supports of the present invention. The selection of an appropriate ligand is within the ability of one skilled in the art.

In another embodiment, proteins containing glutathione-S-transferase (GST) can be purified by contacting the proteins with immobilized glutathione. The proteins are purified as a result of the affinity of the GST for its substrate. Such systems are more fully described in, for example, U.S. Pat. No. 5,654,176, incorporated herein by reference. Thus, in another embodiment, the glutathione is immobilized on the interior surface, or a portion thereof, of the container and/or a bead or other support within the container.

Proteins may also be purified by using biotin or biotin analogs in combination with avidin, streptavidin, or the derivatives of avidin or streptavidin. For example, in one embodiment, when streptavidin is immobilized on the containers and/or supports of the present invention, biotin labeled proteins can be purified based on the affinity of biotin for streptavidin. Similarly, a protein containing a streptavidin tag, such as those described in U.S. Pat. No. 5,506,121, herein incorporated by reference, may be purified based on the affinity of the tag for streptavidin. In another embodiment, when biotin is immobilized on the containers and/or solid supports of the present invention, proteins containing avidin or streptavidin tags may be purified based on the affinity of biotin for avidin and streptavidin. The use of avidin/biotin or biotin/streptavidin affinity purification techniques is well known in the art, and described in, for example, Sambrook and Russell, Molecular Cloning: A Laboratory Manual, 3rd Edition, Cold Spring Harbor Laboratory Press, Cold Spring Harbor, N.Y., 2001.

Proteins and DNA or RNA may also be purified using ion exchange chromatography or hydrophobic chromatography. In ion exchange chromatography, a charged particle immobilized on a solid support binds reversibly to a protein or DNA that has a surface charge. For example, the ion-exchange capture ligand may contain a nitrogen group, a carboxyl group, a phosphate group, or a sulfonic acid group. Examples of ion-exchanger capture ligands include diethylaminoethyl (DEAE), diethyl[2-hydroxypropyl]aminoethyl (QAE), carboxymethyl (CM), and sulfopropyl (SP), and phosphoryl. In hydrophobic chromatography, a protein or DNA with hydrophobic groups on its surface is purified based on hydrophobic interactions with an insoluble hydrophobic group immobilized on a solid support. Examples of hydrophobic ligands are silica, phenyl, hexyl, octyl, and C18 groups. Thus, in one embodiment, charged particles are immobilized on the surface of the containers and/or supports of the present invention. In another embodiment, insoluble hydrophobic groups, are immobilized on the surface of the containers and/or supports of the present invention.

Other suitable capture ligands include, for example, hormones, amino acids, proteins, peptides, polypeptides, lectins, enzymes, enzyme substrates, enzyme inhibitors, cofactors, nucleotides, oligonucleotides (e.g., oligo dT), polynucleotides, carbohydrates, sugars, oligosaccharides, drugs, and dyes.

A variety of other purification techniques are known in the art and may be used in conjunction with the containers and methods of the present invention. Some such techniques are described in, e.g., Kenney & Fowell, Methods in Molecular Biology, Vol. 11, Practical Protein Chromatography (1992); Hanson & Ryden, Protein Purification: Principles, High Resolution Methods, and Applications (1989); Dean, et al., Affinity Chromatography: A Practical Approach (1987); Hermanson, et al., Immobilized Affinity Ligand Techniques (1992); and Jakoby & Wilchek, Affinity Techniques, Enzyme Purification, Part B, in Methods in Enzymology, Vol. 34 (1974).

Once the cellular component is bound to the capture ligand, cellular debris may be washed away, e.g., by using water or buffer. After washing, the bound cellular component may then be released from its association with the capture ligand and removed for characterization or quantitation. Release of the target cellular component may be accomplished using a variety of elution techniques including changes in pH or temperature, or through competitive binding. Specific elution techniques will vary, depending on which capture system is used, but will be readily apparent to those skilled in the art. Alternatively, the captured component may be detected while still attached to the immobilized ligand. A variety of analytical techniques are known, including, for example, ELISA, enzymatic analysis, and protein detection, among others.

Polymeric Coatings

In one embodiment, the capture ligands are bound directly to the interior surface of the container. Alternatively, the capture ligands may be bound to a polymeric matrix that overlies the container surface. Stated differently, the capture ligands may be bound directly to the polymeric matrix which, in turn, is bound to or otherwise immobilized on the interior surface of the container. For example, the capture ligand may be a metal chelating composition which is bound to a derivatized dextran polymer matrix which overlies a polystyrene or other plastic substratum. Polymeric matrices may thus be used to increase the effective surface area (by having a matrix which presents a greater surface area than the underlying substratum), thereby enabling an increased density of capture ligands. Alternatively, or in addition, the polymeric matrix may be more or less hydrophobic than the container wall and thereby present a surface which is desirably more (or alternatively less) hydrophilic than the natural surface of the substratum.

The polymeric coating may be formed or applied by a variety of methods. For example, the polymeric coating may be formed by in situ polymerization; in this approach, a mixture of monomers are dissolved in solvent with an initiator and, after activation, polymerization is carried out on the surface of the container wall. Alternatively, a fully grown polymer may be immobilized on the surface of the container wall. Such approaches are described, for example, in Sundberg et al., U.S. Pat. No. 5,624,711.

In a preferred embodiment in which a polymeric coating is applied, the polymeric coating is derived from a mixture of two polymers that are bound to the container wall. In general, one or both of such polymers contains a reactive group, which when activated, chemically bonds a polymer molecule containing such reactive groups to the container wall and/or crosslinks the molecule with itself or with other polymer molecules. In addition, one or both of such polymers may contain activatable groups that provide points of attachment for the capture ligands described herein. Such polymeric coatings and the means for their formation are generally described in U.S. Patent Application Pub. No. 2003/0032013 A1.

The density of the polymer matrix on the substrate may be controlled by, inter alia, selection and amounts of the particular polymer and reactive groups employed. The molecular weight of the polymer, the number and type of reactive group and the number and molecular weight of the capture ligands may be selected and adjusted, as detailed further below. The polymer matrix may be attached to all of the substrate or to only a part of the substrate. For example, only a portion of the wall of a container or only a fraction of the wells of a multi-well plate may be provided with the polymer matrix.

Polymeric Matrices Formed From Polymer Mixtures

Containers comprising a polymer matrix may be prepared by contacting the container substrate with a polymer composition comprising a plurality of polymer molecules having repeating units, wherein at least some of the polymer molecules have at least one reactive group covalently attached thereto, wherein at least some of the polymer molecules have at least one capture ligand (or activatable group) covalently attached thereto, wherein the polymer molecules have an average molecular weight of at least 100 kDa, and wherein at least 25% of the polymer molecules have at least one reactive group and at least one capture ligand covalently attached thereto. The reactive groups are activated to covalently bind at least some of the polymer molecules directly to the container substrate and to induce cross-linking between polymer molecules to form a polymer matrix attached to the container substrate.

In general, the polymeric matrix may comprise natural polymers (or a derivative thereof), synthetic polymers (or a derivative thereof), a blend of natural polymers (or derivative(s) thereof), a blend of synthetic polymers (or derivative(s) thereof), or a blend of one or more natural polymers (or derivative(s) thereof) and one or more synthetic polymers (or derivative(s) thereof). In general, a natural polymer is a branched or linear polymer produced in a biological system. Examples of natural polymers include, but are not limited to, oligosaccharides, polysaccharides, peptides, proteins, glycogen, dextran, heparin, amylopectin, amylose, pectin, pectic polysaccharides, starch, DNA, RNA, and cellulose. A particular modified natural polymer that may be used is a dextran-lysine derivative produced by covalently inserting lysine into variable linear positions along the dextran molecule using periodate oxidation and reductive amination or other methods known to those of skill in the art. In contrast, synthetic polymers are branched or linear polymers that are manmade. Examples of synthetic polymers include plastics, elastomers, and adhesives, oligomers, homopolymers, and copolymers produced as a result of addition, condensation or catalyst driven polymerization reactions, i.e., condensation polymerization. Whether natural or synthetic, the polymer may be derivatized or modified by oxidation, or by the covalent attachment of photo-reactive groups, affinity ligands, ion exchange ligands, hydrophobic ligands, other natural or synthetic polymers, or spacer molecules.

The polymeric matrix may thus comprise one or more of several distinct polymer types. Exemplary polymers include, but are not limited to, cellulose-based products such as hydroxyethyl cellulose, hydroxypropyl cellulose, carboxymethyl cellulose, cellulose acetate, and cellulose butyrate; acrylics such as those polymerized from hydroxyethyl acrylate, hydroxyethyl methacrylate, glyceryl acrylate, glyceryl methacrylate, acrylic acid, methacrylic acid, acrylamide, and methacrylamide; vinyls such as polyvinyl pyrrolidone and polyvinyl alcohol; nylons such as polycaprolactam, polylauryl lactam, polyhexamethylene adipamide, and polyhexamethylene dodecanediamide; polyurethanes; polylactic acids; linear polysaccharides such as amylose, dextran, chitosan, heparin, and hyaluronic acid; and branched polysaccharides such as amylopectin, hyaluronic acid and hemicelluloses. Blends of two or more different polymer molecules can be used. For example, in one embodiment the polymer molecules are a mixture of dextran and heparin. In another embodiment dextran is mixed with poly Lys-Gly (1 lysine per 20 glycine).

In general, the polymer molecules preferably have an average molecular weight (total molecular weight of polymer, including covalently attached functional groups) of at least 100 kDa. In some embodiments, the polymer molecules have an average molecular weight of 300 kDa to 6,000 kDa. In some embodiments, the polymer molecules have an average molecular weight of 400 kDa to 3,000 kDa. In another embodiment, the polymer molecules have an average molecular weight of 500 kDa to 2,000 kDa, wherever the average molecular weight is the weight average molar mass (Mw) value of a polymer as measured by gel filtration chromatography using multi-angle light scattering and refractive index detection. The average Mw of the polymer distribution of all chain lengths present is based upon the selection of the peak as measured by the refractive index, starting and ending peak selection criteria of a refractive index value that is three times the refractive index baseline. As shown by example a preferred polymer may have an average Mw of 1,117 kDa with a molecular weight range from 112 kDa to 19,220 kDa.

In one embodiment, the polymeric matrix is formed by immobilizing a mixture of polymers wherein a subset of the polymer molecules in the mixture contain capture ligand(s) or activatable group(s) enabling the subsequent covalent attachment of capture ligands and a different subset of the polymer molecules have at least one reactive group covalently attached thereto (for attaching the polymers to the container wall and crosslinking as previously described). This interaction of the reactive group between polymer molecules enables the formation of the three-dimensional matrix. The reactive group reacts either thermochemically or photochemically (polymers that contain a photo-reactive group are referred to as being photolabeled).

When the polymer molecules have capture ligands (or activatable groups) covalently attached, the ratio of capture ligands (or activatable groups) to polymer repeating units is preferably about 1:1 capture to about 1:100, respectively. For example, in one embodiment the ratio of capture ligands (or activatable groups) to polymer repeating units is preferably about 1:1 capture to about 1:20, respectively. When the polymer molecules have reactive groups covalently attached, the ratio of reactive groups to polymer repeat units is preferably less than about 1:600, more preferably, the ratio of reactive groups to polymer repeat units is preferably less than about 1:200 respectively.

Exemplary reactive groups include, but are not limited to, reactive groups used in the preparation of chromatography media which include: epoxides, oxiranes, N-hydroxysuccinimide, aldehydes, hydrazines, maleimides, mercaptans, amino groups, alkylhalides, isothiocyanates, carbodiimides, diazo compounds, tresyl chloride, tosyl chloride, and trichloro-S-triazine. Preferred reactive groups are α, β unsaturated ketone photo-reactive groups. Exemplary photo-reactive groups include aryl azides, diazarenes, beta-carbonyldiazo, and benzophenones. The reactive species are nitrenes, carbenes, and radicals. These reactive species are generally capable of covalent bond formation. Preferred photo-reactive groups are photoactivatable, unsaturated ketones such as acetophenones, benzophenones, and derivatives thereof. A photo-reactive group when contacted with light may become activated, and capable of covalently attaching to the surface of a solid substrate. For example, the photo-reactive groups may be activated by exposure to UV light from about 3 Joules/cm$^2$ to about 6 Joules/cm$^2$ depending on the intensity of light and duration of exposure time. The exposure times may range from as low as 0.5 sec/cm$^2$ to approximately 32 min/cm$^2$ depending on the intensity of the light source. In a preferred embodiment, the photo-reactive groups are activated by exposure to light for 0.5 sec/cm$^2$ to 5 sec/cm$^2$ at about 1,000 mWatts/cm$^2$ to about 5,000 mWatts/cm$^2$, or from about 1,000 mWatts/cm$^2$ to about 3,000 mWatts/cm$^2$, or from about 1,500 mWatts/cm$^2$ to about 2,500 mWatts/cm$^2$.

In one embodiment, capture ligands and/or reactive groups are covalently attached to the polymer molecules via a spacer. When used in connection with the formation of a polymer matrix, a spacer is a molecule or combination of covalently bonded molecules that connect the polymer molecule and either one or more of a capture ligand or reactive group. The spacer can be the same or different from any polymer, polymer composition, or polymer matrix. Those of skill in the art will know that many types of spacers are available and the selection and use is dependent upon the intended application of the polymer matrix, e.g., a lysine molecule or an aminocaproic acid molecule.

The spacer can be covalently attached to the photo-reactive group by a number of different chemistries including amide formation. For example, the use of the hydrocarbon spacer dramatically enhances polymer matrix stability performance. A photo-reactive group with a spacer may be coupled to a portion of a primary amine of the preferred polymer dextran by an amide bond at a controlled ratio relative to total monomer, glucose. Examples of photo-reactive groups with a spacer include, but are not limited to, benzobenzoic aminocaproic, N-Succinimidyl-N'-(4-azido-salicyl)-6-aminocaproate, N-Succinimidyl-(4-azido-2-nitrophenyl)-aminobutyrate, and N-Succinimidyl-(4-azido-2-nitrophenyl)-6-aminocaproate. These photo-reactive groups with spacers may be reacted with a polymer to produce a spacer that now includes the lysine as well as the original spacer attached to the photo-reactive group. The spacer can also be manufactured by incorporating multiple molecules such as lysine and aminocaproic acid prior to attaching the photo-reactive group containing or not containing an additional spacer. An example of a reactive group covalently attached to a polymer molecule is a spacer comprising a moiety or residue of lysine bound to one or more chemical entities of the reactive group, by the loss of a reactive hydrogen from the amino group. In one embodiment, the density of primary amines contributed by the lysine spacers represents the density of desired capture ligand and reactive group.

Modified polymers containing primary amines or other moieties such as spacers in a range of one moiety per every 1 to 100 polymer repeating units may be made by procedures known in the art. Modification of these moieties to selectively incorporate the desired amount of reactive groups is also known. For example, the density of the primary amines contributed by the lysine spacers is on average 1 for every 12 repeating glucose units of the dextran polymer. This density is very high relative to the desired incorporation of photo-reactive groups, e.g., less than one photo-reactive group per 200 repeating monomers. The concentration of primary amines in solution during polymer manufacture might be 4.5 μmoles/mL, whereas the desired incorporation of photo-reactive groups would represent 0.09 μmoles/mL. Therefore, in this instance, there would be a 50-fold excess of primary amine to the required photo-reactive group incorporation via a reactive ester. At this concentration of amine, the addition of photo-reactive group via a reactive ester at the desired level of incorporation results in greater than 90% efficiency of incorporation. By varying the amount of photo-reactive group containing a reactive ester any incorporation level less than 1 reactive group per 200 monomers can be consistently achieved. The method required to efficiently convert each of the remaining spacer moieties or amines to capture ligand attachment points is known in the art. A several fold excess of an amine reactive, e.g., reactive ester, derivatization reagent is used for the attachment of the capture ligand, either directly in one step or through multiple steps. In some cases, the derivatization reagent will present an additional reactive group which, depending on its reactivity, will dictate the stoichiometry for subsequent capture ligand attachment. When lower ligand density is desired the initial amine reactive derivatization reagent will be lowered accordingly. In some instances free amines remaining after selective modifications will generally be derivatized by acetylation.

The first step in coating a surface of a substrate is contacting the polymer composition with the substrate surface to be coated. The method used to contact the polymer composition with the container surface depends on the dimensions and shape of the surface to be coated. The container may be made from a variety of natural and synthetic materials, such as those listed above. The container surface can be derivatized prior to coating. Pre-derivatization can be done by any method known by one of skill in the art, including silanization of silica and glass and plasma treatment of polystyrene or polypropylene to incorporate amines, carboxyl groups, alcohols, aldehydes and other reactive groups or by chemical modification of the surface to change its chemical composition.

If necessary, the surface of the substrate may be chemically modified to facilitate covalent bonding with the reactive groups carried on the polymer molecules. Such modifications include treating the substrate surface with a hydrocarbon, or plasma-treating the surface. An illustrative example of a chemical modification is the silanization of glass. In a preferred embodiment a MALDI plate is dipped into a 1 mg/mL solution of parafilm dissolved in chloroform and dried.

When coating a multiwell plate, tube or a surface or a portion thereof, larger than 0.1 mm square, the polymer composition may be contacted with the container surface by pouring, micropipeting, or transferring the polymer composition onto the portions of the container or plate, e.g., wells, to be coated. In the alternative, the portion of the plate, tube, container surface, or support larger than 2 mm square to be coated may also be coated by dipping the portion of the surface into a solution of the polymer composition so as to place the container surface in contact with the polymer composition.

The amount of polymer that attaches to the container surface may be adjusted or controlled by varying the polymer composition concentration and volume added to the substrate. Once the polymer composition is placed in contact with the surface, the polymer composition may be dried on the container surface prior to activating the reactive groups, for example, evaporated to dryness by incubation in the dark at 20-50° C. with air flow. The polymer composition can also be evaporated using lyophilization or by any other drying means, including air drying, to remove the solvent. A variety of drying methods may be used provided that there is no premature activation of the reactive groups in response to the drying step. The substrate is considered sufficiently dry when no moisture is detectable visibly. During the drying, the polymer molecules of the polymer composition orient themselves so as to bind with the substrate surface or interact with each other to promote inter and intra-crosslinking with other polymers of the polymer composition.

The dried coated solid surface is then treated to induce the reactive groups to covalently bond to the substrate. In the case of the photo-reactive groups, they may be activated by irradiation. Activation is the application of an external stimulus that causes reactive groups to bond to the substrate. Specifically, a covalent bond is formed between the substrate and the reactive group, e.g., carbon-carbon bond formation.

There are many UV irradiation systems capable of delivering the total energy (dosage measured in Joules) required to bond the photo-activated polymer to a hydrocarbon rich substrate. Irradiation may be provided by a mercury lamp which has a distinct and known wavelength pattern of irradiation. The intensity of irradiation required is from about 3 to about 6 $J/cm^2$. Joule measurements encompass the time factor (1 Joule=Watt×second). In one embodiment, the irradiation is provided by an electrodeless mercury lamp powered by microwave radiation. One six inch, 500 W/in. lamp has a rated power output of 2,500 $mW/cm^2$ measured in the UVA range at about 2 in distance of lamp to substrate. The lamp can be successfully run at 80% power or approximately 2,000 $mW/cm^2$. Sample plates prepared using a standard low intensity UV irradiation box having an intensity of irradiation (UVA/UVB, approximately 250 to 350 nm) measured at approximately 9.0 $mW/cm^2$ and requiring greater than 10 $J/cm^2$ (10,000 mJ) total energy to provide good bonding. This requires an incubation time of the sample plates in the irradiation box of greater than 20 min. Plates processed using an electrodeless mercury lamp (2,000 $mW/cm^2$) irradiation system requires only 1.75 $sec/cm^2$ for a total energy dosage of 3.5 $J/cm^2$. The higher intensity irradiation more efficiently activates the photo-active groups and consequently a lower overall energy dosage is required.

In one embodiment, activation may be done with a UVA/UVB light irradiating at 9.0 $mW/cm^2$ for approximately 30 min to a total energy of approximately 15,000 $mJ/cm^2$. In a preferred embodiment, activation may be done by exposure to UVA/UVB light irradiating at 2,000 $mW/cm^2$ to a total energy of from about 3 $J/cm^2$ to about 4 $J/cm^2$. The amount of incubation time and the total energy used may vary according to the photo-reactive group bound to the polymer. In the most preferred embodiment, activation may be done by photoirradiation using a Fusion UV Conveyor System using a mercury electrodeless lamp irradiating at 2,000 $mW/cm^2$ with the conveyer belt set at 8 ft/min with the lamp power at 400 W/in. A radiometer, IL290 Light Bug, is run through the conveyer belt to verify the desired energy in the range of 3,000-4,000 $mJ/cm^2$. The multiwell plates, for example, are photoirradiated at about 800 plates per hour, or about 1 plate per 4 to 5 seconds.

The concentration of the polymer composition can be adjusted by changing the amount of total polymer per milliliter of solvent. In the case where a higher concentration of polymer composition or polymer matrix per square centimeter would be advantageous, less solvent can be used to solvate the polymer molecules of the composition. In the case where a lower concentration of polymer composition or polymer matrix per square centimeter would be advantageous, more solvent can be used to solvate the polymer molecules of the composition. In other words, adjusting the concentration of the polymer composition between 0.02 and 1.0 mg/mL solvent and coating a solid surface, such as a multiwell plate, would produce a surface having a selectable range of total bound polymer matrix. The polymer composition can be completely soluble or contain suspended insoluble polymer. The solvents that may be used to make the polymer composition include water, alcohols, ketones, and mixtures of any or all of these. The solvent(s) are preferably compatible with the substrate being used. Since the polymers of the composition may crosslink between each other, it is possible that a fluid-like solution of the composition may change into a gel. In the alternative, the solution may be produced in the form of a slurry. Examples of solvents that may be used in the composition include water, alcohols, ketones, and mixtures of any or all of these.

Non-bound polymers may be removed by incubating in a suitable solution to dissolve and remove unbound polymer. For example, multiwell plates may be incubated with MOPS buffer overnight at 25° C., washed with MPTS buffer and distilled water three times each, washed with hibitane solution, air dried, packaged and stored below ambient temperature (2-8° C.). The remaining polymers form the polymer matrix.

The resulting polymer-coated substrate preferably contains the polymer matrix in a density of at least 2 µg/cm², more preferably, in a density of 4 µg/cm² to 30 µg/cm², and, for some embodiment, in a density of 6 µg/cm² to 15 µg/cm². The density of capture ligands (or activatable groups) in the polymer matrix may thus be controlled by controlling the number and/or molecular weight of the capture ligands covalently attached to the polymer molecules. Generally the density of capture ligands (or activatable groups) in the polymer matrix is preferably at least 1 nanomole/cm². In some embodiments, the density of the capture ligands (or activatable groups) is about 1.2 nanomoles/cm² to about 185 nanomoles/cm². In another embodiment, the density of the capture ligands (or activatable groups) is about 1.5 nanomoles/cm² to about 90 nanomoles/cm², or about 1.8 nanomoles/cm² to about 15 nanomoles/cm². As a result, the polymer matrix may thereby enable binding target molecules having a molecular weight of less than 3.5 kDa in an amount of at least 1 nanomole/cm².

In a preferred embodiment, the polymer molecules contacted with the container substrate have at least one capture ligand (or activatable group) covalently attached thereto and at least some of the polymer molecules have no reactive group covalently attached thereto. The percentage of polymer molecules having both reactive groups and capture ligands covalently attached may be 25% to 80%. In another embodiment the percentage of both reactive groups and capture ligands attached may be from 40% to 75%. In yet another embodiment, the percentage of both reactive groups and capture ligands attached may be from 50% to 60%. In a preferred embodiment, the percentage of polymer molecules having both reactive groups and capture ligands covalently attached thereto may be approximately 50%. The use of a mixture of polymer molecules, with and without reactive groups, enhances the highly functional formation of a three dimensional polymer matrix.

If desired, the capture ligands in the formed polymer matrix may be derivatized, e.g., by noncovalently or covalently attaching the capture ligands either by the addition of a different capture ligand or chemical modification of the existing capture ligand, thereby further enabling the high capacity capture of a larger variety of target molecules.

In one embodiment, the container is a multiwell polystyrene plate, the polymer coating is derived from a mixture of dextran polymers, the capture ligand is a nickel chelate, and the polymer matrix has a capture ligand density of 1.5 nanomoles/cm² to 7.5 nanomoles/cm². In other embodiments, the capture ligand is a Gallium or Iron chelate or the capture ligand is glutathione. In one exemplary alternative of this embodiment, the polymer and capture ligand have the following formula:

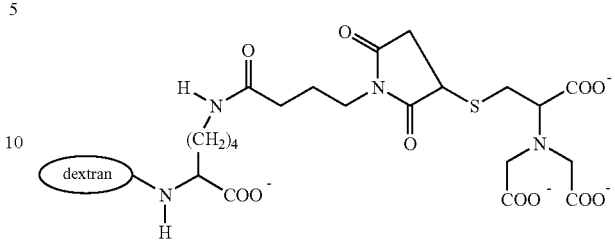

In an alternative embodiment, the container is a multiwell polypropylene plate, the polymer coating is derived from a mixture of dextran polymers, and the capture ligand is an oligonucleotide.

In yet another alternative embodiment, the container is a multiwell polystyrene plate, the polymer coating is derived from a mixture of dextran polymers, the capture ligand is streptavidin, and the polymer matrix has a capture ligand density of 1.5 µg/cm² to 7.5 µg/cm².

Additionally, in another embodiment, the container is a multiwell polystyrene plate, the polymer coating is derived from a mixture of dextran polymers, the capture ligand is selected from the group consisting of protein A, protein G, protein L, or a mixture thereof, and the polymer matrix has a capture ligand density of 1.5 µg/cm² to 7.5 µg/cm².

In another embodiment, the container is a polypropylene column, the polymer coating is derived from a mixture of dextran polymers, and the capture ligand is a nickel chelate.

A container comprising a polymer matrix, as detailed above, can be used in combination with the detergent compositions described in greater detail elsewhere herein to lyse cells and isolate target cellular components from the resulting solutions. The detergent composition may be provided within the container in any suitable manner, such as those described above. In one embodiment, the detergent composition is adsorbed onto at least a portion of the polymer matrix. In another embodiment, the detergent composition resides within the container as a free-flowing powder, on top of the polymer matrix. A solution comprising host cells may then be added to the container comprising the polymer matrix and the detergent composition. Once some or all of the cellular components have been released from a host cell by the detergent composition, the target cellular component may be isolated from the cellular solution by the capture ligand present in the polymer matrix.

The polymer matrix may be constructed to enable binding target molecules having a molecular weight of 3.5 kDa to 500 kDa in an amount of 0.5 µg/cm² to 20 µg/cm², a molecular weight of 10 kDa to 500 kDa in an amount of 1 µg/cm² to 20 µg/cm², a molecular weight of 10 kDa to 350 kDa in an amount of 2 µg/cm² to 20 µg/cm², a molecular weight of 10 kDa to 350 kDa in an amount of 3 µg/cm² to 15 µg/cm². In some embodiments, the polymer matrix is capable of binding target molecules with a molecular weight of 10 kDa to 350 kDa in an amount of 4 µg/cm² to 10 µg/cm². In certain embodiments the polymer matrix is capable of binding polypeptide target molecules having a molecular weight up to 350 kDa in an amount of at least 2 µg/cm² of polymer matrix.

Methods for Extraction or Extraction and Isolation of Target Products

In general, the methods of the present invention are directed to the extraction or extraction and isolation of a target product, such as a peptide, protein, nucleic acid, or other cellular component, from a host cell. Thus, in one aspect, the present invention is directed to a process for the extraction of a cellular component from a host cell, the process comprising (a) introducing a liquid suspension containing the host cell into a well, the well having a mouth, an interior surface, a volume, V, and a coating of a detergent composition on at least a portion of the interior surface, the interior surface comprising a sidewall formation and a bottom, the ratio of the area of the coated interior surface to the volume, V, being less than about 4 mm$^2$/μl, and (b) lysing the host cell in the container to release the cellular component and form cellular debris. The detergent composition causes the host cell to release its contents. Lysis may be complete, i.e., all the cellular components (e.g., peptides, proteins, or nucleic acids) are released from the host cell, or partial, i.e., a portion of the cellular components are released from the host cell.

In another aspect, the present invention is directed to a process for the extraction and isolation of a cellular component from a host cell. In one aspect, the process comprises (a) introducing a liquid suspension containing the host cell into a well, the well having a mouth, an interior surface, a volume, V, a detergent composition, and a supported, capture ligand, the interior surface comprising a sidewall formation and a bottom, the sidewall formation being between the bottom and the mouth, the mouth serving as the inlet for the introduction of the liquid into and the outlet for the removal of the liquid from the well, (b) lysing the host cell in the well to release the cellular component and form solid cellular debris; and (c) capturing the cellular component with the capture ligand in the presence of the solid cellular debris. In one embodiment, the capture ligand is supported by the interior surface of the container. In another embodiment, the capture ligand is attached to a polymeric matrix coated on the interior surface of the container.

In another aspect, the process comprises (a) introducing a liquid suspension containing the host cell into a well, the well having a mouth, an interior surface, a volume, V, a detergent composition, and a supported capture ligand, the interior surface comprising a sidewall formation and a bottom, the sidewall formation being between the bottom and the mouth, the mouth serving as the inlet for the introduction of the liquid into the well, (b) lysing the host cell in the well to release the cellular component and form solid cellular debris; (c) capturing the cellular component with the capture ligand in the presence of the solid cellular debris, (d) releasing the cellular component from the capture ligand, and (e) recovering the released cellular component. In one embodiment, the capture ligand is supported by the interior surface of the container. In another embodiment, the capture ligand is attached to a polymeric matrix coated on the interior surface of the container.

Lysis may be complete, i.e., all the cellular components are released from the host cell, or partial, i.e., a portion of the cellular components are released from the host cell. In one embodiment, the cellular debris and other unbound cellular compositions are then washed away, leaving the cellular component attached to the capture ligand. The captured product may then be detected while still attached to the capture ligand. Such detection methods are well known in the art, and include ELISA, protein detection, and enzymatic analysis, among others. In another embodiment, the captured component is recovered by releasing or eluting the captured cellular component from the capture ligand, through the use of reagents such as salts, or by the competitive binding of other reagents with the capture ligands.

In another embodiment, the methods described above may be performed in a well or wells of a multiwell plate, such as a 96 well multiwell plate, comprising a detergent composition and a polymer matrix coating. For example, in one embodiment, the well(s) is coated with a polymer matrix such as the polymer matrix previously described, to which is attached a capture ligand. In a preferred embodiment, the polymer matrix is derived from a mixture of dextran polymers, and the capture ligand is a nickel chelate. In one embodiment, the detergent composition is comprised of 3-(N,N-Dimethyltetradecylammonio)propanesulfonate and 3-(4-Heptyl)phenyl-3-hydroxypropyl)dimethylammoniopropanesulfonate. More specifically, the detergent composition may be comprised of 1.0% (w/v) 3-(N,N-Dimethyltetradecylammonio)propanesulfonate and 0.1% (w/v) 3-(4-Heptyl)phenyl-3-hydroxypropyl)dimethylammoniopropanesulfonate. In one embodiment, the detergent composition is coated onto at least a portion of the surface of the polymer matrix and/or onto the sidewalls of the well(s). Alternatively, or in addition, the detergent composition may be present in the form of a free-flowing powder within the well(s). Upon addition of a liquid suspension containing host cells into the well(s), the detergent composition is dissolved, and the host cells are lysed, as previously described. The target cellular component is then bound by the capture ligand. The captured target cellular component may then optionally be released and recovered using techniques known in the art and previously described.

In another aspect, the present invention is directed to a process for the preparation of a multiwell plate for the extraction of a cellular component from a host cell. The process comprises contacting the interior surfaces of a plurality of the wells of the multiwell plate with a liquid containing a detergent composition, and drying the liquid to form an adsorbed layer of detergent composition on the interior surfaces of the wells. Any detergent composition, as described herein, can be used in this manner. As previously discussed, the amount of detergent composition may vary, but should be sufficient so that the amount of adsorbed detergent composition will provide the desired level of extraction. Drying may be accomplished by air drying, use of an incubator, or other techniques known in the art.

Containers for the extraction and isolation of a cellular component from a host cell may be prepared in a similar manner. For example, in one embodiment, the interior surface of a well comprising a supported capture ligand may be contacted with a liquid containing a detergent composition, and the liquid dried to form an adsorbed layer of detergent composition on the interior surface of the well. In another embodiment, the interior surface of a well comprising a polymer matrix attached thereto (e.g. a well or wells of a multiwell plate, described above) may be contacted with a liquid containing a detergent composition, and the liquid dried to form an adsorbed layer of detergent composition on the surface of the polymer matrix and/or the sidewalls of the well(s). In another embodiment, the interior surface of a column, such as a column comprising a resin with attached capture ligands, as described above, may be contacted with a liquid containing a detergent composition, and the liquid dried to form an adsorbed layer of detergent composition on the surface of the resin and/or the sidewalls of the column.

Kits

Advantageously, a container of the present invention may be combined with instructions for use, and reagents for extracting and/or isolating a cellular component from a host cell, and/or reagents for assaying or detecting a captured cellular component, and/or processing buffers or controls, wherein all of this is packaged together and distributed as a kit. In one embodiment, the kit would comprise a single container or, alternatively, a multiwell plate comprising a plurality of containers; typically, the kit will be sealed. Either way, a detergent composition is included, and, optionally, a capture ligand may also be included.

As described herein, the detergent composition and/or capture ligand may be provided in a container of the present invention in a variety of different manners. For example, the detergent composition may be coated on a portion of the container, on the bottom of the container, on the sidewall formation, on both the bottom and the sidewall formation of the container, or may be present in the form of a free-flowing powder.

Likewise, a supported capture ligand may be positioned on a portion of the container, on the bottom of the container, on the sidewall formation, or on both the bottom and the sidewall formation of the container. In one embodiment, the container further comprises an additional support, such as a bead or mesh, onto which a detergent composition may be coated and/or a supported capture ligand may be positioned. Alternatively, the container may be a high capacity platform comprising a three dimensional polymer matrix, a capture ligand or activatable group, and a detergent composition.

In one embodiment, the container will comprise all reagents necessary for the extraction or extraction and isolation of the target product (e.g., polypeptide, protein, RNA or DNA product). The kit may also contain other reagents and equipment useful in releasing or eluting the captured product from the supported capture ligands or three dimensional matrix, as well as various processing buffers.

All publications, patents, patent applications and other references cited in this application are herein incorporated by reference in their entirety as if each individual publication, patent, patent application or other reference were specifically and individually indicated to be incorporated by reference.

DEFINITIONS

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "capture ligand" means any moiety, molecule, receptor, or layer that can be or is immobilized or supported on a container or support and used to isolate a cellular component from cellular debris. Some non-limiting examples of capture ligands that may be used in connection with the present invention include: biotin, streptavidin, various metal chelate ions, antibodies, various charged particles such as those for use in ion exchange chromatography, dye, various affinity chromatography supports, and various hydrophobic groups for use in hydrophobic chromatography.

The terms "cell debris" and "cellular debris" are used interchangeably herein to describe membrane fragments, organelles, or any other soluble or insoluble cell component other than a target product, that is released from the host cell as a result of cell lysis.

The term "extraction" means the release of at least some of the target product from the host cell in which it is expressed, as a result of cell lysis.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring.

The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "host cell" means any prokaryotic or eukaryotic cell that expresses or contains the target product. Host cells may include, for example, bacterial cells, such as E. coli; fungal cells, such as yeast cells; plant cells; animal cells, such as mammalian cells; and insect cells.

The term "isolation" or "purification" means the removal or separation of at least a portion of the target product from at least part of the cellular debris.

The term "lysis" or "lysing" means rupturing the cell wall and/or cell membrane of a cell so that the target product is released. Lysis may be complete or partial (i.e., the cell wall and/or cell membrane is rendered sufficiently permeable to release some, but not necessarily all of its cellular components).

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "target product" means any cellular component, such as a polypeptide, protein, protein fragment, DNA, RNA, other nucleotide sequence, carbohydrate, lipid, cholesterol, kinase, or other cellular component, that is to be extracted or extracted and isolated from the host cell in which it is expressed or contained (e.g., the "target protein," "target DNA," "target RNA," "target cellular component," etc.). The target product may naturally occur in the host cell, or it may be non-naturally occurring, e.g., a recombinant protein.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate the invention.

Example 1

Preparation of MAT-Tagged GST Expressing Bacterial Cells

Cell Growth. Five ml of previously sterilized Terrific Broth (Sigma-Aldrich Co. Product No. T9179) was placed into two 15-ml round bottom tubes. Ampicillin (Sigma-Aldrich Co. Product No. A9518) was added to each tube to a final concentration of 0.1 mg/ml. A 20 µl aliquot of a glycerol stock solution of BL21 E. coli expressing metal affinity tag (MAT)-tagged GST was added to the first tube. A 20 µl aliquot of a glycerol stock solution of BL21 E. coli expressing FLAG-tagged GST was added to the second tube. The cultures were incubated overnight at 37° C. with shaking at 275 RPM.

The starter cultures that were grown overnight were used to inoculate two 500-ml autoclaved Terrific Broth (TB) samples. Ampicillin was added to a final concentration of 0.1 mg/ml to the flasks. The cultures were incubated for 3 hours at 37° C. with shaking at 275 RPM. Isopropyl β-1-thiogalactopyranoside (IPTG) was added to the cultures at a final concentration of 1 mM to induce expression of the target proteins. The cultures were incubated another 4 hours at 37° C. with shaking at 275 RPM. The cells were transferred to two 500 ml centrifuge bottles and pelleted by spinning at 2,000×g for 20 minutes. The supernatants were discarded and the pellets were saved for future experiments.

Example 2

Extraction and Purification of MAT-Tagged GST Using Detergent Lysis Solutions

This example sets forth results that compare a zwitterionic detergent combination of the present invention with a commercially available lysis solution, CelLytic B (Sigma-Aldrich Co. Product No. B3553). This reagent contains 1% (w/v) octyl-β-D-thioglucopyranoside, with a Tris buffer. The soluble protein fraction is extracted using a detergent lysis solution, and then affinity purified using HIS-Select Nickel Spin Columns (Sigma-Aldrich Co. Product No. H7787).

Preparation of Lysis Solutions. The zwitterionic detergent combination of the current invention was prepared by dissolving 10 grams of 3-(N,N-Dimethyltetradecylammonio) propanesulfonate (Sigma-Aldrich Co. Product No. T7763) and 1 gram of C7BzO (Sigma-Aldrich Co. Product No. C0856) into 100 ml of ultrapure water ("CelLytic 10× Lysis Reagent"). The "Tris Working Reagent" was prepared by diluting 1 ml of the CelLytic 10× Lysis Reagent into 8.6 ml of ultrapure water and 400 µl of 1M Tris solution. The "Phosphate Working Reagent" was prepared by diluting 1 ml of the CelLytic 10× Lysis Reagent into 5 ml of 2× Saline Solution (600 mM NaCl, 100 mM sodium phosphate, pH 8.0) and 4 ml of ultrapure water.

Cell Lysis. Three 0.5 gram samples of the bacterial cell pellet were placed into separate 15 ml tubes. The first pellet was dissolved in 5 ml of CelLytic B. The second pellet was dissolved in 5 ml of the "Tris Working Reagent." The third pellet was dissolved in 5 ml of "Phosphate Working Reagent." Samples were incubated with mixing for 10 minutes at room temperature. All three samples were clarified by centrifugation at 16,000×g for 12 minutes. The supernatants were saved, and the pellet discarded.

Figure 2:
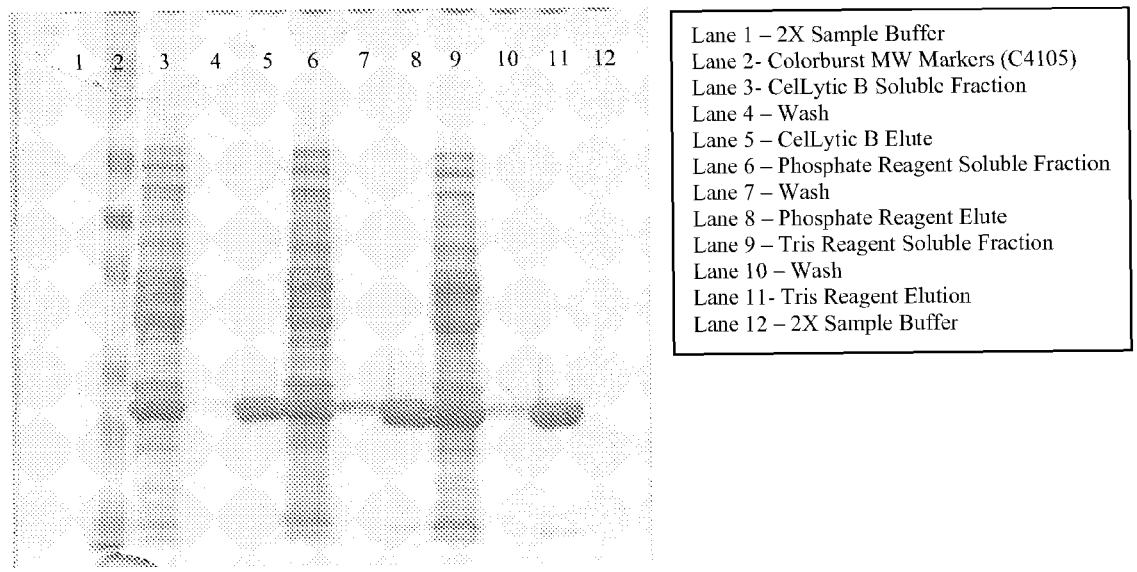
FIG. 2 is an image of a SDS-PAGE gel depicting the extraction and purification of a his-tagged protein from a recombinant E. coli cell paste using different extraction reagents. The proteins were purified using HIS-Select Spin Columns (Sigma-Aldrich Co. Product No H7787) after host cells were lysed with the commercially available CelLytic B (Sigma-Aldrich Co. Product No. B3553), the zwitterionic detergent combination of 3-(N,N-Dimethyltetradecylammonio)propanesulfonate (Sigma-Aldrich Co. Product No. T7763) and C7BzO (Sigma-Aldrich Co. Product No. C0856) in either a Tris based buffer (i.e., "Tris Working Reagent") or a phosphate based buffer (i.e., "Phosphate Working Reagent"). The contents of each lane are listed on the right of the gel image.

GST-MAT Purification. Nine HIS-Select Spin Columns (Sigma-Aldrich Co. Product No. H7787) were equilibrated with 600 µl of HIS-Select Wash Buffer (300 mM NaCl, 50 mM sodium phosphate, pH 8.0, 5 mM imidazole). The protein was bound to the spin columns by adding 600 µl of the respective clarified lysis solution to the top of the column, and centrifuging for 1 minute at 2,000 RPM×g for 2 minutes. Columns 1-3 were used for purifying soluble GST-MAT extracted using CelLytic B. Columns 4-6 were used for purifying soluble GST-MAT extracted using the "Tris Working Reagent." Columns 7-9 were used for purifying soluble GST-MAT extracted using the "Phosphate Working Solution." After collecting the unbound material, the spin columns were washed by adding 600 µl of HIS-Select Wash Buffer to the top of the column and centrifuging at 2,000×g for 2 minutes. The wash step was repeated once. The spin columns were eluted by adding 500 µl of HIS-Select Elution Buffer (300 mM NaCl, 50 mM sodium phosphate, pH 8.0, 250 mM imidazole) and centrifuging at 2,000×g for 2 minutes. The amount of protein eluted from each spin column was measured using Bradford reagent (Sigma-Aldrich Co. Product No. B6916), and is indicated in FIG. 1. Samples were mixed 1:1 with Laemmli Sample Buffer (Sigma-Aldrich Co. Product No. S3401) and a 10 µl sample was run on a 4-20% Tris-glycine gel. The gel is shown in FIG. 2.

Example 3

Extraction and Purification of MAT-Tagged GST and FLAG-Tagged GST Using Detergent Lysis Solutions Preparation of Lysis Solutions. "Tris Working Reagent" was prepared as indicated above. BugBuster 10× was obtained from Novagen. BugBuster working reagent was prepared by diluting 1 ml of BugBuster 10× into 8.6 ml of ultrapure water and 400 µl of a 1M Tris-HCl, pH 8.0 solution.

Cell Lysis. Two 0.35 gram samples of the bacterial cell pellet expressing FLAG-tagged GST were placed into separate 15 ml tubes. The first pellet was dissolved in 3.5 ml of "Tris Working Reagent." The second pellet was dissolved in 3.5 ml of the BugBuster working reagent (as prepared above). Two 0.65 gram samples of the bacterial cell pellet expressing MAT-tagged GST were placed in separate tubes. The first pellet was dissolved in 6.5 ml of "Tris Working Reagent." The second pellet was dissolved in 6.5 ml of the BugBuster working reagent. The samples were incubated, with mixing, for 10 minutes at room temperature. The samples were then clarified by centrifugation at 16,000×g for 12 minutes. The supernatants were saved, and the pellet discarded. From each detergent lysis, the soluble fraction from the MAT-tagged GST extraction was split into two equal parts.

Figure 3:
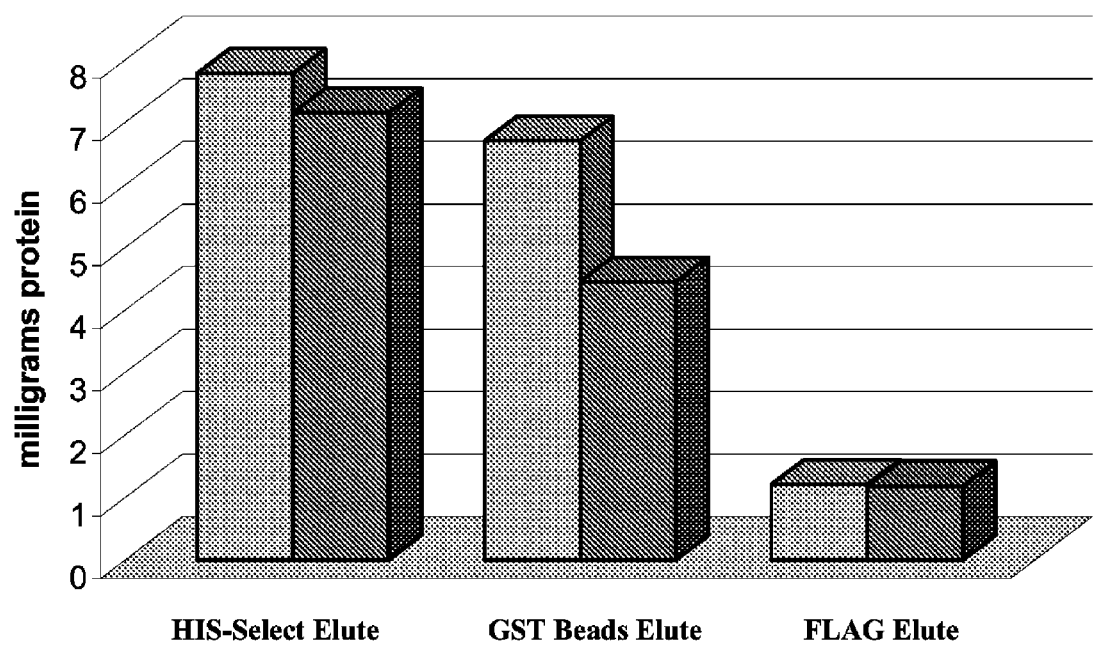
FIG. 3 depicts a graph comparing the amount of protein recovered from host cells that were lysed with either the zwitterionic detergent combination of 3-(N,N-Dimethyltetradecylammonio)propanesulfonate (Sigma-Aldrich Co. Product No. T7763) and C7BzO (Sigma-Aldrich Co. Product No. C0856) in a Tris based buffer (i.e., "Tris Working Reagent") (light gray bars) or with the commercially available product BugBuster® (dark gray bars). Lysed samples were then affinity purified using HIS-Select nickel affinity gel, GST agarose gel or anti-FLAG M2 affinity gel.

GST-MAT Purification. Two 500 µl aliquots of Glutathione Magnetic Beads (Sigma-Aldrich Co., Product No. G1919) were equilibrated in TBS (50 mM Tris, 138 mM NaCl, 27 mM KCl, pH 8.0). Two 500 µl samples of HIS-Select Nickel Affinity gel were equilibrated in HIS-Select Wash Buffer (300 mM NaCl, 50 mM sodium phosphate, pH 8.0, 5 mM imidazole). Half of the soluble protein fraction obtained from the BugBuster clarified GST-MAT lysate (as prepared above) was loaded onto one sample of the Glutathione Magnetic Beads. The other half was loaded onto one sample of the HIS-Select Nickel Affinity Gel. Half of the soluble protein fraction obtained from the "Tris Working Reagent" clarified GST-MAT lysate (as prepared above) was loaded onto one sample of the Glutathione Magnetic Beads. The other half was loaded onto one sample of the HIS-Select Nickel Affinity Gel. The Glutathione Magnetic Beads samples were washed with 5 ml of TBS, pH 8.0, and eluted with 2.5 ml of TBS, pH 8.0, 10 mM reduced glutathione. Total protein in the elution was quantified using Bradford reagent. The HIS-Select Nickel Affinity Gel samples were washed with 5 ml of HIS-Select Wash Buffer, and eluted with 2.5 ml of HIS-Select Elution Buffer (300 mM NaCl, 50 mM sodium phosphate, pH 8.0, 250 mM imidazole). Total protein in the elution was quantified using Bradford reagent the results are illustrated in FIG. 3.

FLAG-GST Purification. Two 1 ml aliquots of ANTI-FLAG M2 Agarose (Sigma-Aldrich Co. Product No. A2220) were equilibrated in 10 ml of PBS (120 mM NaCl, 2.7 mM KCl, 10 mM phosphate salts, pH 7.4). The soluble protein fraction obtained from the BugBuster clarified FLAG-GST lysate (as prepared above) was loaded onto one sample of the Anti-FLAG M2 Agarose. The soluble protein fraction obtained from the "Tris Working Reagent" clarified FLAG-GST lysate (as prepared above) was loaded onto the other sample of ANTI-FLAG M2 Agarose. Both resin samples were washed with 20 ml of PBS. The samples were eluted with 5 ml of 0.1 M Glycine, pH 3.0. Total protein was quantified using Bradford reagent and the results are shown in FIG. 3.

Example 4

Comparison of Detergent vs. Mechanical Lysis For Extraction and Purification of GST-MAT Preparation of Lysis Solutions. "Tris Working Reagent" was prepared as indicated above. B-PER was obtained from Pierce Chemical Company (Rockford, Ill.).

Cell Lysis. Three 0.2 gram samples of the bacterial cell pellet expressing MAT-tagged GST were placed into separate 15 ml tubes. The first pellet was dissolved in 2.0 ml of "Tris Working Reagent." The second pellet was dissolved in 2.0 ml of B-PER. These two samples were incubated, with mixing, for 10 minutes at room temperature. The third sample was resuspended in 2.0 ml of HIS-Select Column Buffer (300 mM NaCl, 50 mM sodium phosphate, pH 8.0) and sonicated on ice using four 15-second bursts. All three samples were clarified by centrifugation at 16,000×g for 12 minutes. The supernatants were saved, and the pellet discarded.

Figure 4:
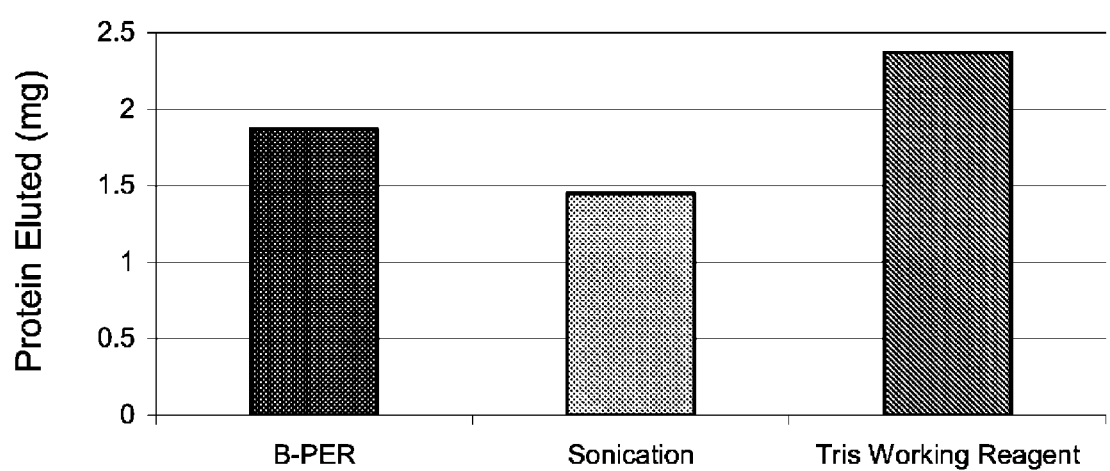
FIG. 4 depicts a graph comparing the amount of protein recovered from host cells that were sonicated or that were lysed with either the commercially available product B-PER or the zwitterionic detergent combination of 3-(N,N-Dimethyltetradecylammonio)propanesulfonate (Sigma-Aldrich Co. Product No. T7763) and C7BzO (Sigma-Aldrich Co. Product No. C0856) in a Tris based buffer (i.e., "Tris Working Reagent"). Samples were affinity purified using HIS-Select nickel affinity gel.

GST-MAT Purification. Three separate 50 µl samples of HIS-Select Nickel Affinity Gel were equilibrated in HIS-Select Column Buffer. Each of the soluble protein fractions obtained from the cell lysis step above were loaded onto a sample of the equilibrated HIS-Select resin, and incubated with mixing for 30 minutes at room temperature. Following centrifugation to collect the resin, the unbound protein fraction was removed. The resins were washed with 1 ml of HIS-Select Wash Buffer, and eluted with 500 µl of HIS-Select Elution Buffer. Total protein in the elution was quantified using Bradford reagent and is shown in FIG. 4.

Example 5

Detergent Lysis, Capture and Purification of Recombinant Proteins Using High Capacity and High Sensitivity HIS-Select™ and ANTI-FLAG® M2 Plates In this example, bacterial cells expressing a target protein with a DYKDDDDK (SEQ. ID. NO. 1) and/or his tag were lysed using various detergent(s) in combination with processing aids, and the target protein was purified in one step. Unless otherwise noted, all materials were obtained from Sigma-Aldrich Corporation, St. Louis, Mo.

Dry Lysis Support. Various combinations of detergents, processing reagents, and enzymes were used to examine a range of lysis conditions. Detergent lysis solutions containing the following were prepared:
  a) 2% SB 3-10, 0.2% C7BzO, 0.2% n-dodecyl α-D-maltoside, 0.2% Triton X-100
  b) 2% CHAPS, 1% ASB-14
  c) 2% SB 3-14, 0.2% C7BzO
  d) 2% CHAPS, 1% n-Octyl glucoside
  e) 2% SB 3-12, 0.2% C7BzO
  f) 2% SB 3-14, 0.2% ASB-14
  g) 1% n-Octyl glucoside, 1% CHAPS, 0.2% n-dodecyl α-D-maltoside
  h) 8% CHAPS The detergent CHAPS is 3-[(3-cholamidopropyl)dimethylammonio]-1-propanesulfonate; SB3-10 is 3-(decyldimethylammonio)propanesulfonate inner salt; SB3-12 is 3-(dodecyldimethylammonio)propanesulfonate inner salt; SB3-14 is 3-(N,N-dimethylmyristylammonio)propanesulfonate; C7BzO is 3-(4-heptyl) phenyl 3-hydroxy propyl)dimethylammonio propane sulfonate; and ASB-14 is 3-[N,N-dimethyl(3-myristoylaminopropyl)ammonio]propanesulfonate.

The first seven detergent solutions (a-g) also contained 40 mM Tris-HCl, pH 7.4, 0.04% lysozyme (Sigma L3790), and 0.01% Benzonase® endonuclease (Sigma E1014). The 8% CHAPS solution (h) also contained 80 mM Tris-HCl, pH 8.0, 0.04% lysozyme (Sigma L6876), and 0.01% DNase I (Sigma D4527). 100 µl of each of these detergent solutions was dispensed into 6 wells (half a row) of a HIS-Select™ high capacity plate (Sigma M5563), HIS-Select™ high sensitivity plate (Sigma S5688), ANTI-FLAG® M2 high capacity plate, and an ANTI-FLAG® M2 high sensitivity plate (Sigma P2983). The lytic reagents were dried overnight in an incubator with ambient air running over the plates.

Cell Growth. 5-ml sterile terrific broth (TB) was added to each of three 15 ml round bottom tubes. Ampicillin was added to a final concentration of 0.1 mg/ml to each of the tubes. A 20 µl aliquot of a glycerol stock solution of BL21 E. coli expressing a target protein with a DYKDDDDK (SEQ. ID. NO. 1) tag was added to the first tube. A 20 µl aliquot of a glycerol stock solution of BL21 E. coli expressing a target protein with a DYKDDDDK (SEQ. ID. NO. 1)/his tag was added to the second tube. A 20 µl aliquot of a glycerol stock solution of BL21 E. coli expressing a target protein with a his tag was added to the third tube. The cultures were incubated overnight at 37° C. with shaking at 275 rpm.

The starter cultures grown overnight were used to inoculate three 500-ml autoclaved terrific broth samples. Ampicillin was added to a final concentration of 0.1 mg/ml to each flask. The cultures were incubated for 4 hours at 37° C. with shaking at 275 rpm. Isopropyl β-D-1-thiogalactopyranoside (IPTG) was added to the cultures at a final concentration of 1 mM to induce expression of the target proteins. The cultures were incubated another 3 hours at 37° C. with shaking at 275 rpm.

E. coli Samples. E. coli expressing the recombinant proteins grown in the 500 ml shake flasks was added to two columns of each plate that was coated with the lysis reagents, in 200 µl aliquots. The empty wells were used as controls. The samples were incubated at room temperature for 2 hours with gentle shaking.

Enzyme Immunodetection Assay for High Sensitivity Plates. The wells were washed 4 times with TBS-T, pH 8.0, followed by 4 washes with deionized water, using a BioTek plate washer. 200 µl of a horseradish peroxidase (HRP) conjugated antibody specific to the target protein was added to each well. The plates were allowed to incubate with the antibody for 45 minutes at room temperature, and then were washed 4 times with TBS-T, pH 8.0. 100 µl of TMB substrate (Sigma T0440) was added to each well and the plates were developed until the color was distinct. At this point, the reaction was stopped by adding 100 µl of 1M HCl to each well. Absorbance readings were obtained at 450 nm, and the blanks were subtracted to determine corrected $A_{450}$.

TCA Precipitation for High Capacity Plates. The wells were washed 4 times with TBS-T, pH 8.0, followed by 4 washes with deionized water, using a BioTek plate washer. 100 µl of 50 mM sodium phosphate, pH 8.0, 300 mM NaCl, and 250 mM imidazole was aliquoted into each well of the HIS-Select™ high capacity plate. 100 µl of 0.1 M glycine, pH 3.0, was aliquoted into each well of the ANTI-FLAG® M2 high capacity plate. The plates were allowed to incubate at 37° C. for 20 minutes to elute the target proteins. The eluted samples were removed from the plates and placed into clean tubes. Each sample was diluted with 0.2% sodium deoxycholate solution (Sigma D3691) to a final volume of 500 µl. The samples were briefly vortexed and incubated at room temperature for 10 minutes. 50 µl of a 100% trichloroacetic acid solution (TCA) (Sigma T6323) was added to each sample, and they were briefly vortexed and incubated on ice for 15 minutes. The samples were centrifuged at 15,000×g for 10 minutes at room temperature and the supernatants were decanted off. 500 µl of a 25% acetone solution (Sigma A5351) was added to each tube. The samples were briefly vortexed and centrifuged at 15,000×g for 5 minutes. The supernatants were decanted off and the protein pellets were dried in a SpeedVac at 30° C. for 20 minutes.

SDS-PAGE Analysis. Each protein pellet was resuspended in 10 µl of Laemmli sample buffer (Sigma S3401), and titrated to basic pH with 1 M NaOH. 10 µl of each sample was electrophoresed through 10-20% Tris-glycine gels (BioRad Cat. #345-0044). The gels were stained with EZ Blue™ (Sigma G1041) gel staining reagent for 1 hour, and destained with deionized water overnight.

Figure 5:
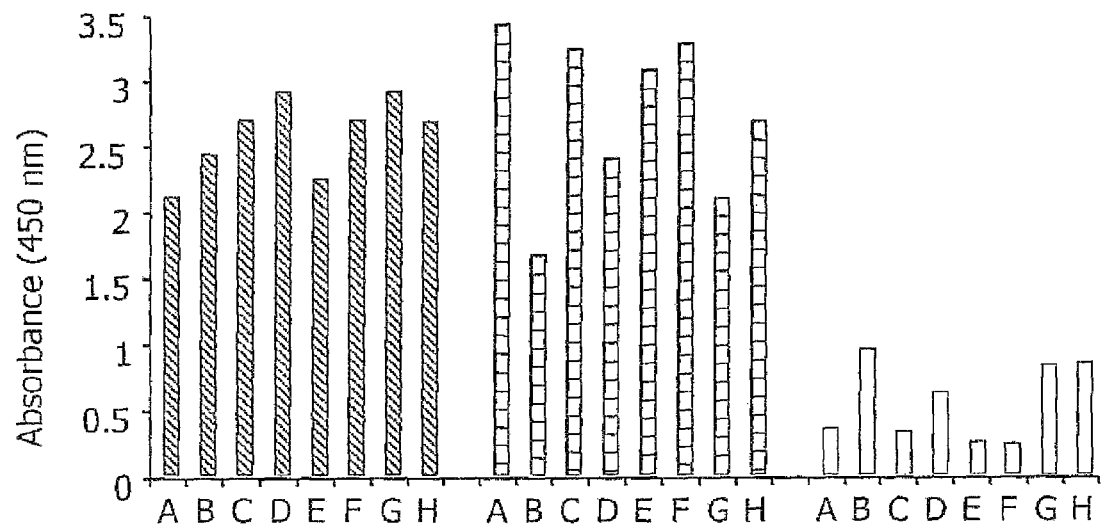
FIG. 5 depicts corrected absorbance ($A_{450}$) readings from an enzyme immunodetection assay using an ANTI-FLAG® M2 high sensitivity plate. The striped bars on the chart represent results for proteins with a DYKDDDDK (SEQ. ID. NO. 1) tag; the bars with horizontal lines represent results for proteins with a DYKDDDDK (SEQ. ID. NO. 1)/his tag; the white bars represent results for proteins with a his-tag. The lytic reagents used are described in Example 5, and represented on the chart by the letters A-H.
Figure 6:
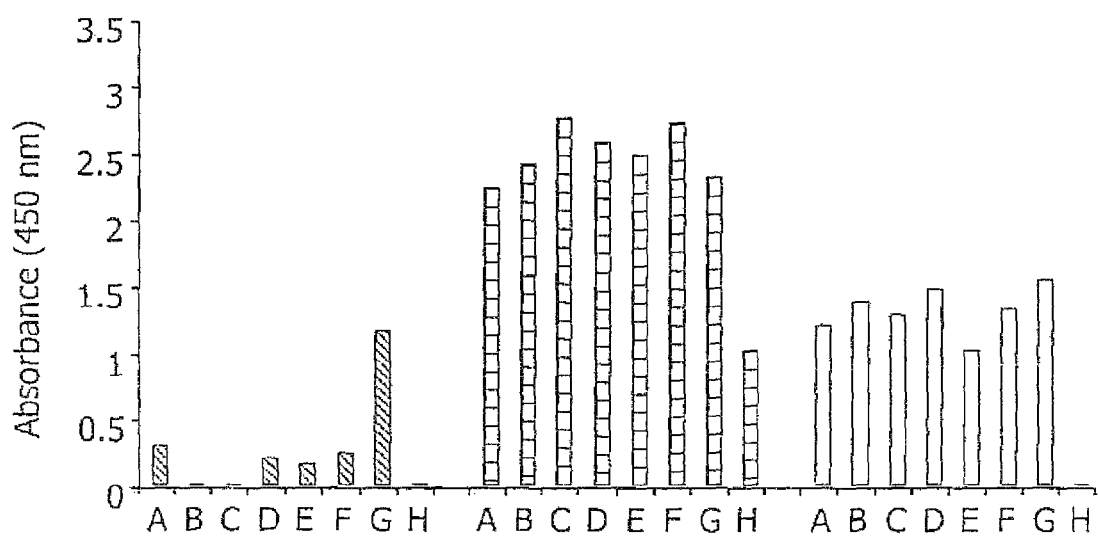
FIG. 6 depicts corrected absorbance ($A_{450}$) readings from an enzyme immunodetection assay using a HIS-Select™ high sensitivity plate. The striped bars on the chart represent results for proteins with a DYKDDDDK (SEQ. ID. NO. 1) tag; the bars with horizontal lines represent results for proteins with a DYKDDDDK (SEQ. ID. NO. 1)/his tag; the white bars represent results for proteins with a his-tag. The lytic reagents used are described in Example 5, and represented on the chart by the letters A-H.
Figure 7:
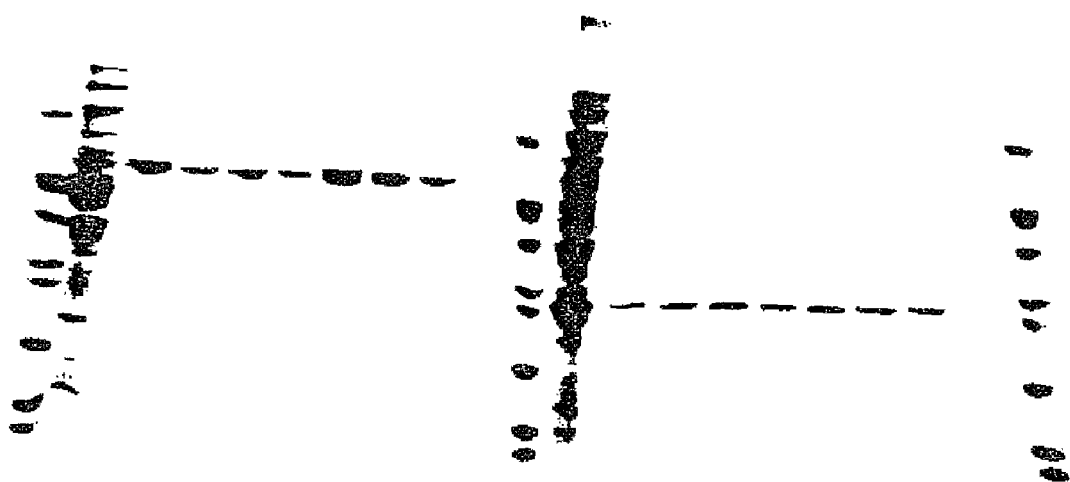
FIG. 7 depicts an image of a SDS-PAGE gel of material that was eluted from a HIS-Select™ high capacity plate. Various combinations of lytic reagents, processing reagents, and enzymes were dried onto the surface of a HIS-Select™ high capacity plate, and cells comprising a target protein were added. The contents of each lane are described in Table D. This figure illustrates that the various lysis reagents were capable of lysing the cells, and that the target protein was successfully captured and eluted from the HIS-Select™ high capacity plate.

Results and Discussion. The corrected $A_{450}$ readings from the enzyme immunodetection assay indicated that the target protein was successfully captured on the HIS-Select™ and ANTI-FLAG® M2 high sensitivity plates. The various detergent formulations were capable of lysing the cells, allowing the protein to be captured. FIG. 5 depicts the corrected absorbance values from the ANTI-FLAG® M2 high sensitivity plate assay, which shows that the proteins with a DYKDDDDK (SEQ. ID. NO. 1) tag were captured, while those proteins without a DYKDDDDK (SEQ. ID. NO. 1) tag were not. FIG. 6 contains corrected absorbance values from the HIS-Select™ high sensitivity plate immunodetection assay, and shows that the plate was capable of selectively capturing his-tagged target proteins, while not capturing proteins without a his-tag. Similarly, the SDS-PAGE results in FIG. 7 show that the target protein was successfully captured and eluted from the HIS-Select™ high capacity plate. Similar results were obtained from the ANTI-FLAG® M2 high capacity plate. Table D indicates the lysing reagent and composition of the sample used for each lane in FIG. 7.

TABLE D

Lytic Reagent and Sample Composition for SDS-PAGE Analysis

| Lane Number | Lysis Reagent in Plate | Composition of Sample |
|---|---|---|
| 1 | N/A | Molecular Weight Markers (Sigma Product M3913) |
| 2 | N/A | 10 µl E. coli cells expressing ~60 kDa his-tagged protein |
| 3 | 1% SB 3-10, 0.1% C7BzO, 0.1% n-dodecyl α-D-maltoside, 0.1% Triton X-100, 20 mM Tris-HCl, pH 7.4, 0.02% lysozyme, 0.005% Benzonase ® endonuclease (Sigma E1014) | Sample eluted from HIS-Select™ High Capacity plate with imidazole |
| 4 | 1% CHAPS, 0.5% ASB-14, 20 mM Tris-HCl, pH 7.4, 0.02% lysozyme, 0.005% Benzonase ® endonuclease (Sigma E1014) | Sample eluted from HIS-Select™ High Capacity plate with imidazole |
| 5 | 1% SB 3-14, 0.1% C7BzO, 20 mM Tris-HCl, pH 7.4, 0.02% lysozyme, 0.005% Benzonase ® endonuclease (Sigma E1014) | Sample eluted from HIS-Select™ High Capacity plate with imidazole |
| 6 | 1% CHAPS, 0.5% n-Octyl glucoside, 20 mM Tris-HCl, pH 7.4, 0.02% lysozyme, 0.005% Benzonase ® endonuclease (Sigma E1014) | Sample eluted from HIS-Select™ High Capacity plate with imidazole |
| 7 | 1% SB 3-12, 0.1% C7BzO, 20 mM Tris-HCl, pH 7.4, 0.02% lysozyme, 0.005% Benzonase ® endonuclease (Sigma E1014) | Sample eluted from HIS-Select™ High Capacity plate with imidazole |
| 8 | 1% SB 3-14, 0.1% ASB-14, 20 mM Tris-HCl, pH 7.4, 0.02% lysozyme, 0.005% Benzonase ® endonuclease (Sigma E1014) | Sample eluted from HIS-Select™ High Capacity plate with imidazole |
| 9 | 0.5% n-Octyl glucoside, 0.5% CHAPS, 0.1% n-dodecyl α-D-maltoside, 20 mM Tris-HCl, pH 7.4, 0.02% lysozyme, 0.005% Benzonase ® endonuclease (Sigma E1014) | Sample eluted from HIS-Select™ High Capacity plate with imidazole |
| 10 | 4% CHAPS, 40 mM Tris-HCl, pH 8.0, 0.02% lysozyme, 0.005% DNase I (Sigma D4527) | Sample eluted from HIS-Select™ High Capacity plate with imidazole |
| 11 | N/A | Molecular Weight Markers (Sigma Product M3913) |
| 12 | N/A | 10 µl E. coli cells expressing ~24 kDa his-tagged protein |

TABLE D-continued

Lytic Reagent and Sample Composition for SDS-PAGE Analysis

| Lane Number | Lysis Reagent in Plate | Composition of Sample |
|---|---|---|
| 13 | 1% SB 3-10, 0.1% C7BzO, 0.1% n-dodecyl α-D-maltoside, 0.1% Triton X-100, 20 mM Tris-HCl, pH 7.4, 0.02% lysozyme, 0.005% Benzonase ® endonuclease (Sigma E1014) | Sample eluted from HIS-Select ™ High Capacity plate with imidazole |
| 14 | 1% CHAPS, 0.5% ASB-14, 20 mM Tris-HCl, pH 7.4, 0.02% lysozyme, 0.005% Benzonase ® endonuclease (Sigma E1014) | Sample eluted from HIS-Select ™ High Capacity plate with imidazole |
| 15 | 1% SB 3-14, 0.1% C7BzO, 20 mM Tris-HCl, pH 7.4, 0.02% lysozyme, 0.005% Benzonase ® endonuclease (Sigma E1014) | Sample eluted from HIS-Select ™ High Capacity plate with imidazole |
| 16 | 1% CHAPS, 0.5% n-Octyl glucoside, 20 mM Tris-HCl, pH 7.4, 0.02% lysozyme, 0.005% Benzonase ® endonuclease (Sigma E1014) | Sample eluted from HIS-Select ™ High Capacity plate with imidazole |
| 17 | 1% SB 3-12, 0.1% C7BzO, 20 mM Tris-HCl, pH 7.4, 0.02% lysozyme, 0.005% Benzonase ® endonuclease (Sigma E1014) | Sample eluted from HIS-Select ™ High Capacity plate with imidazole |
| 18 | 1% SB 3-14, 0.1% ASB-14, 20 mM Tris-HCl, pH 7.4, 0.02% lysozyme, 0.005% Benzonase ® endonuclease (Sigma E1014) | Sample eluted from HIS-Select ™ High Capacity plate with imidazole |
| 19 | 0.5% n-Octyl glucoside, 0.5% CHAPS, 0.1% n-dodecyl α-D-maltoside, 20 mM Tris-HCl, pH 7.4, 0.02% lysozyme, 0.005% Benzonase ® endonuclease (Sigma E1014) | Sample eluted from HIS-Select ™ High Capacity plate with imidazole |
| 20 | 4% CHAPS, 40 mM Tris-HCl, pH 8.0, 0.02% lysozyme, 0.005% DNase 1 (Sigma D4527) | Sample eluted from HIS-Select ™ High Capacity plate with imidazole |
| 21 | N/A | Molecular Weight Markers (Sigma Product M3913) |

What is claimed is:

1. A method for extracting a target product from a host cell, the method comprising:
   (a) contacting the host cell with a detergent composition comprising at least two different compounds, each of the two compounds having at least one quaternary amine and at least one sulfonate ion, the ratio of one compound to the other compound being from about 5:1 to about 20:1 (w/v); and
   (b) lysing the host cell to release the target product from the cell and form cellular debris.

2. The method of claim 1, wherein each of the two compounds of the detergent composition has a formula selected from the group consisting of formula (Ia), formula (Ib) and formula (Ic):

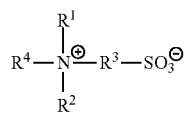
(Ia)

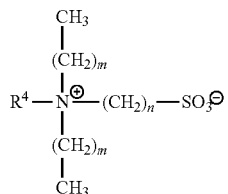
(Ib)

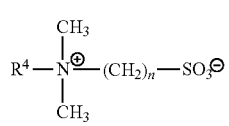
(Ic)

wherein:
   m is an integer from 0 to 10;
   n is an integer from 1 to 10; and
   $R^1$, $R^2$, $R^3$, and $R^4$ are independently hydrocarbyl or substituted hydrocarbyl.

3. The method of claim 2, wherein the detergent composition comprises 3-(N,N-dimethyltetradecylammonio)propanesulfonate and 3-(4-heptyl)phenyl-3-hydroxypropyl)dimethylammoniopropanesulfonate.

4. The method of claim 1, wherein the contacting comprises introducing a liquid suspension containing the host cell into a well containing the detergent composition.

5. The method of claim 4, wherein each of the two compounds of the detergent composition has a formula selected from the group consisting of formula (Ia), formula (Ib) and formula (Ic):

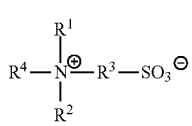
(Ia)

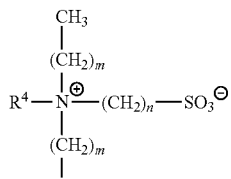
(Ib)

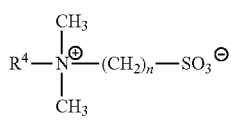
(Ic)

wherein:
   m is an integer from 0 to 10;
   n is an integer from 1 to 10; and
   $R^1$, $R^2$, $R^3$, and $R^4$ are independently hydrocarbyl or substituted hydrocarbyl.

6. The method of claim 4, wherein the detergent composition is coated onto at least a portion of the interior surface of the well or is in the form of a free flowing powder contained in the well.

7. The method of claim 4, further comprising isolating the target product from the host cell by capturing the target product with a capture ligand in the presence of the cellular debris.

8. The method of claim 7, wherein the capture ligand is selected from the group consisting of a metal chelate, glutathione, biotin, streptavidin, an antibody, a charged particle, and an insoluble hydrophobic group.

9. The method of claim 8, wherein the capture ligand is an antibody specific for a sequence selected from the group consisting of SEQ ID NO: 1, SEQ ID NO: 2, and SEQ ID NO: 3.

10. The method of claim 8, wherein the capture ligand is a metal chelate derived from a composition having the formula:

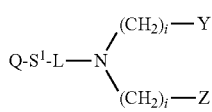

wherein:
   Q is a carrier;
   $S^1$ is a spacer;
   L is -A-T-CH(X)— or —C(=O)—;
   A is an ether, thioether, selenoether, or amide linkage;
   T is a bond or substituted or unsubstituted alkyl or alkenyl;
   X is —$(CH_2)_kCH_3$, —$(CH_2)_kCOOH$, —$(CH_2)_kSO_3H$, —$(CH_2)_kPO_3H_2$, —$(CH_2)_kN(J)_2$, or —$(CH_2)_kP(J)_2$, preferably —$(CH_2)_kCOOH$ or —$(CH_2)_kSO_3H$;
   k is an integer from 0 to 2;
   J is hydrocarbyl or substituted hydrocarbyl;
   Y is —COOH, —H, —$SO_3H$, —$PO_3H_2$, —$N(J)_2$, or —$P(J)_2$, preferably, —COOH;
   Z is —COOH, —H, —$SO_3H$, —$PO_3H_2$, —$N(J)_2$, or —$P(J)_2$, preferably, —COOH; and
   i is an integer from 0 to 4, preferably 1 or 2.

11. The method of claim 8, wherein the detergent composition comprises 3-(N,N-dimethyltetradecylammonio)propanesulfonate and 3-(4-heptyl)phenyl-3-hydroxypropyl)dimethylammoniopropanesulfonate and the capture ligand is a metal chelate or an antibody.

12. The method of claim 7, wherein the well further comprises a polymer matrix attached to at least a portion of the interior surface of the well, wherein the polymer matrix comprises at least one capture ligand or activatable group covalently attached thereto, and wherein the detergent composition is coated onto at least a portion of the surface of the polymer matrix.

13. The method of claim 12, wherein the polymer matrix is derived from a plurality of polymers, and wherein at least one reactive group is covalently attached to a subset of the polymers, and at least one capture ligand or activatable group is covalently attached to a different subset of polymers.

14. A well for the extraction of a target product from a host cell, the well containing a detergent composition, the detergent composition comprising at least two different compounds, each of the two compounds having at least one quaternary amine and at least one sulfonate ion, the ratio of one compound to the other compound being from about 5:1 to about 20:1 (w/v).

15. The well of claim 14, wherein each of the two compounds of the detergent composition has a formula selected from the group consisting of formula (Ia), formula (Ib) and formula (Ic):

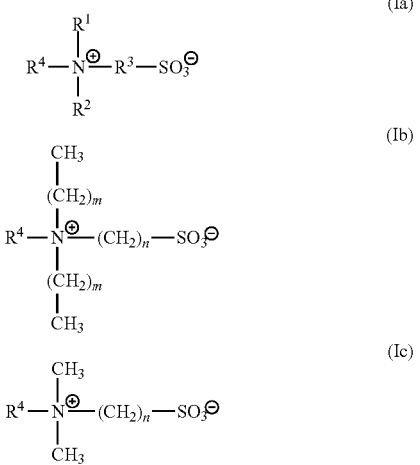

wherein:
m is an integer from 0 to 10;
n is an integer from 1 to 10; and
$R^1$, $R^2$, $R^3$, and $R^4$ are independently hydrocarbyl or substituted hydrocarbyl.

16. The well of claim 14, wherein the detergent composition is coated onto at least a portion of the interior surface of the well or is in the form of a free flowing powder contained in the well.

17. The well of claim 14, wherein the well further comprises a capture ligand specific for the target product.

18. The well of claim 17, wherein the capture ligand is selected from the group consisting of a metal chelate, glutathione, biotin, streptavidin, an antibody, a charged particle, and an insoluble hydrophobic group.

19. The well of claim 18, wherein the capture ligand is an antibody specific for a sequence selected from the group consisting of SEQ ID NO: 1, SEQ ID NO: 2, and SEQ ID NO: 3.

20. The well of claim 18, wherein the capture ligand is a metal chelate derived from a composition having the formula:

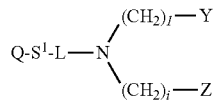

wherein:
Q is a carrier;
$S^1$ is a spacer;
L is -A-T-CH(X)— or —C(=O)—;
A is an ether, thioether, selenoether, or amide linkage;
T is a bond or substituted or unsubstituted alkyl or alkenyl;
X is —$(CH_2)_kCH_3$, —$(CH_2)_kCOOH$, —$(CH_2)_kSO_3H$, —$(CH_2)_kPO_3H_2$, —$(CH_2)_kN(J)_2$, or —$(CH_2)_kP(J)_2$, preferably —$(CH_2)_kCOOH$ or —$(CH_2)_kSO_3H$;
k is an integer from 0 to 2;
J is hydrocarbyl or substituted hydrocarbyl;
Y is —COOH, —H, —$SO_3H$, —$PO_3H_2$, —$N(J)_2$, or —$P(J)_2$, preferably, —COOH;
Z is —COOH, —H, —$SO_3H$, —$PO_3H_2$, —$N(J)_2$, or —$P(J)_2$, preferably, —COOH; and
i is an integer from 0 to 4, preferably 1 or 2.

21. The well of claim 18, wherein the detergent composition comprises 3-(N,N-dimethyltetradecylammonio)propanesulfonate and 3-(4-heptyl)phenyl-3-hydroxypropyl)dimethylammoniopropanesulfonate and the capture ligand is a metal chelate or an antibody.

22. The well of claim 17, wherein the well further comprises a polymer matrix attached to at least a portion of the interior surface of the well, wherein the polymer matrix comprises at least one capture ligand or activatable group covalently attached thereto, and wherein the detergent composition is coated onto at least a portion of the surface of the polymer matrix.

23. The well of claim 22, wherein the polymer matrix is derived from a plurality of polymers, and wherein at least one reactive group is covalently attached to a subset of the polymers, and at least one capture ligand or activatable group is covalently attached to a different subset of polymers.

24. The well of claim 23, wherein the polymers are dextran polymers.

25. The method of claim 3, wherein the ratio of 3-(N,N-dimethyltetradecylammonio)propanesulfonate to 3-(4-heptyl)phenyl-3-hydroxypropyl)dimethylammoniopropanesulfonate is from about 5:1 to about 20:1.

26. The method of claim 25, wherein the ratio is about 10:1.

27. The method of claim 11, wherein the ratio of 3-(N,N-dimethyltetradecylammonio)propanesulfonate to 3-(4-heptyl)phenyl-3-hydroxypropyl)dimethylammoniopropanesulfonate is from about 5:1 to about 20:1.

28. The method of claim 27, wherein the ratio is about 10:1.

* * * * *

UNITED STATES PATENT AND TRADEMARK OFFICE
CERTIFICATE OF CORRECTION

PATENT NO. : 7,897,376 B2  
APPLICATION NO. : 11/850813  
DATED : March 1, 2011  
INVENTOR(S) : Jeff Porter et al.

Page 1 of 1

It is certified that error appears in the above-identified patent and that said Letters Patent is hereby corrected as shown below:

Col. 50, Claim 20, line 10, that portion of the formula reading "$(CH_2)_1$" should read -- $(CH_2)_i$ --

Signed and Sealed this  
Twenty-second Day of November, 2011

David J. Kappos  
*Director of the United States Patent and Trademark Office*